US010799131B2

(12) United States Patent
McKinney et al.

(10) Patent No.: US 10,799,131 B2
(45) Date of Patent: Oct. 13, 2020

(54) CATHETER FOR MONITORING INTRAUTERINE PRESSURE TO PROTECT THE FALLOPIAN TUBES

(71) Applicant: Sentinel Medical Technologies, LLC, Boca Raton, FL (US)

(72) Inventors: Timothy McKinney, Boca Raton, FL (US); Marc-Alan Levine, Pottstown, PA (US)

(73) Assignee: Sentinel Medical Technologies, LLC, Boca Raton, FL (US)

( * ) Notice: Subject to any disclaimer, the term of this patent is extended or adjusted under 35 U.S.C. 154(b) by 308 days.

(21) Appl. No.: 15/978,072

(22) Filed: May 11, 2018

(65) Prior Publication Data
US 2018/0344183 A1    Dec. 6, 2018

Related U.S. Application Data

(63) Continuation-in-part of application No. 15/949,022, filed on Apr. 9, 2018.
(Continued)

(51) Int. Cl.
*A61B 5/00*    (2006.01)
*A61B 5/03*    (2006.01)
(Continued)

(52) U.S. Cl.
CPC ............ *A61B 5/035* (2013.01); *A61B 5/4325* (2013.01); *A61B 5/6853* (2013.01);
(Continued)

(58) Field of Classification Search
CPC ..... A61B 5/035; A61B 5/4325; A61B 5/6853; A61M 25/10; A61M 25/0032; A61M 2025/0002
See application file for complete search history.

(56) References Cited

U.S. PATENT DOCUMENTS 3,721,229 A    3/1973    Panzer
4,192,319 A    3/1980    Hargens et al.
(Continued)

FOREIGN PATENT DOCUMENTS

CA    2961757    3/2016
CN    205649494    10/2016
(Continued)

OTHER PUBLICATIONS

Devoe, LD, et al. "Monitoring intrauterine pressure during active labor. A prospective comparison of two methods", J Reprod Med. Oct. 1989; 34(10): 811-814.
(Continued)

*Primary Examiner* — Max F Hindenburg
(74) *Attorney, Agent, or Firm* — Neil D. Gershon

(57) ABSTRACT

A multi-lumen catheter for monitoring intrauterine pressure comprising an elongated body configured and dimensioned for insertion into a uterus of a patient, the catheter having a first lumen, a second lumen, and a first balloon at a distal portion. The first lumen communicates with the first balloon and the second lumen has an opening within the uterus for injection of x-ray dye or other fluid into the uterus for imaging the uterine cavity and the fallopian tubes of a patient. The first balloon contains a gas to form along with the first lumen a chamber to monitor pressure within the uterus to thereby determine if excessive pressure is being applied to the fallopian tubes of the patient. A sensor is in communication with the first lumen to measure pressure about a circumferential area of the balloon to measure pressure in the uterus to provide readings of intrauterine pressure.

16 Claims, 23 Drawing Sheets

Related U.S. Application Data

(60) Provisional application No. 62/622,871, filed on Jan. 27, 2018, provisional application No. 62/590,513, filed on Nov. 24, 2017, provisional application No. 62/544,690, filed on Aug. 11, 2017, provisional application No. 62/514,793, filed on Jun. 3, 2017.

(51) Int. Cl.
  *A61M 25/10* (2013.01)
  *A61M 25/00* (2006.01)

(52) U.S. Cl.
  CPC ......... *A61M 25/0032* (2013.01); *A61M 25/10* (2013.01); *A61M 2025/0002* (2013.01)

(56) References Cited

U.S. PATENT DOCUMENTS

| | | | |
|---|---|---|---|
| 4,739,769 A | 4/1988 | Matthews et al. | |
| 4,873,986 A | 10/1989 | Wallace | |
| 4,901,731 A | 2/1990 | Millar | |
| 5,167,237 A | 12/1992 | Rabin | |
| 5,447,497 A | 5/1995 | Sogard et al. | |
| 5,433,216 A | 7/1995 | Sugrue | |
| 5,551,439 A | 9/1996 | Hickey | |
| 5,570,671 A | 11/1996 | Hickey | |
| 5,573,007 A | 11/1996 | Bobo, Sr. | |
| 5,697,375 A | 12/1997 | Hickey | |
| 5,707,358 A | 1/1998 | Wright | |
| 5,951,497 A | 9/1999 | Wallace et al. | |
| 5,980,485 A | 11/1999 | Grantz et al. | |
| 5,984,879 A | 11/1999 | Wallace et al. | |
| 6,021,781 A | 2/2000 | Thompson et al. | |
| 6,183,421 B1 | 2/2001 | Bobo | |
| 6,231,524 B1 | 5/2001 | Wallace et al. | |
| 6,434,418 B1 | 8/2002 | Neal et al. | |
| 6,447,462 B1 | 8/2002 | Wallace et al. | |
| 6,461,332 B1 | 10/2002 | Mosel et al. | |
| 6,648,879 B2 | 11/2003 | Joye et al. | |
| 6,673,022 B1 | 1/2004 | Bobo et al. | |
| 6,723,053 B2 | 4/2004 | Ackerman et al. | |
| 6,827,710 B1 | 12/2004 | Mooney et al. | |
| 7,347,822 B2 | 3/2008 | Brockway et al. | |
| 7,381,190 B2 | 6/2008 | Sugrue et al. | |
| 7,654,967 B2 | 2/2010 | Bobo, Sr. | |
| 7,722,544 B2 | 5/2010 | Williams et al. | |
| 8,192,368 B2 | 6/2012 | Woodruff et al. | |
| 8,235,426 B2 | 8/2012 | Pisula, Jr. et al. | |
| 8,337,411 B2 | 12/2012 | Nishtala et al. | |
| 8,360,988 B2 | 1/2013 | Bobo, Sr. et al. | |
| 8,403,884 B2 | 3/2013 | Nishtala | |
| 8,535,237 B2 | 9/2013 | Nishtala | |
| 8,596,688 B2 | 12/2013 | Pisula, Jr. et al. | |
| 8,636,724 B2 | 1/2014 | Wiita et al. | |
| 8,646,325 B2 | 2/2014 | Hoem et al. | |
| 8,708,927 B2 | 4/2014 | Dijkman | |
| 8,876,729 B2 | 11/2014 | Bobo, Sr. et al. | |
| 9,046,205 B2 | 6/2015 | Whitaker et al. | |
| 9,101,314 B2 | 8/2015 | Shi | |
| 9,126,008 B2 | 9/2015 | Kim | |
| 9,393,353 B2 | 7/2016 | Alam et al. | |
| 9,439,600 B2 | 9/2016 | Mohl | |
| 9,440,043 B2 | 9/2016 | Arora et al. | |
| 9,510,766 B2 | 12/2016 | Weed et al. | |
| 9,511,209 B2 | 12/2016 | Drasler et al. | |
| 9,534,721 B2 | 1/2017 | Lombardi, III | |
| 9,622,670 B2 | 4/2017 | Burnett et al. | |
| 9,623,201 B2 | 4/2017 | Gregory et al. | |
| 9,655,555 B2 | 5/2017 | Burnett et al. | |
| 9,662,058 B2 | 5/2017 | Burnett et al. | |
| 9,662,670 B2 | 5/2017 | Veis et al. | |
| 9,695,966 B2 | 7/2017 | Lombardi, III et al. | |
| 9,734,706 B2 | 8/2017 | Moon et al. | |
| 9,931,044 B2 | 4/2018 | Burnett et al. | |
| 9,931,122 B2 | 4/2018 | Burnett et al. | |
| 10,004,551 B2 | 6/2018 | Burnett | |
| 10,238,307 B2 | 3/2019 | Schlumpf et al. | |
| 10,433,741 B2 | 10/2019 | Stimpson | |
| 2002/0183628 A1 | 12/2002 | Reich et al. | |
| 2003/0060800 A1 | 3/2003 | Ryan | |
| 2003/0114835 A1 | 6/2003 | Noda | |
| 2004/0127813 A1 | 7/2004 | Schwamm | |
| 2004/0171942 A1 | 9/2004 | Ackerman et al. | |
| 2005/0055043 A1 | 3/2005 | Foltz | |
| 2005/0065408 A1 | 3/2005 | Benderev | |
| 2005/0187430 A1 | 8/2005 | Aundal et al. | |
| 2005/0240211 A1 | 10/2005 | Sporri | |
| 2005/0283092 A1 | 12/2005 | Gedebov | |
| 2007/0083126 A1 | 4/2007 | Marko et al. | |
| 2007/0282219 A1 | 12/2007 | Holte | |
| 2008/0027358 A1 | 1/2008 | Gregersen et al. | |
| 2008/0077043 A1 | 3/2008 | Malbrain et al. | |
| 2008/0103408 A1 | 5/2008 | Denton et al. | |
| 2008/0146990 A1 | 6/2008 | Jenson et al. | |
| 2009/0221993 A1 | 9/2009 | Sohi et al. | |
| 2010/0056952 A1 | 3/2010 | Liu | |
| 2010/0094204 A1 | 4/2010 | Nishtala | |
| 2010/0094328 A1 | 4/2010 | O'dea et al. | |
| 2010/0113939 A1 | 5/2010 | Mashimo et al. | |
| 2010/0249663 A1 | 9/2010 | Nishtala | |
| 2012/0041334 A1 | 2/2012 | Goedje et al. | |
| 2012/0130272 A1* | 5/2012 | Layton | A61B 5/035 600/560 |
| 2012/0179063 A1 | 7/2012 | Bharucha et al. | |
| 2012/0316460 A1 | 12/2012 | Stout | |
| 2012/0316461 A1 | 12/2012 | Liu | |
| 2013/0030262 A1 | 1/2013 | Burnett et al. | |
| 2013/0066166 A1 | 3/2013 | Burnett et al. | |
| 2013/0079662 A1 | 3/2013 | Damaser et al. | |
| 2014/0155745 A1 | 6/2014 | Duncan | |
| 2014/0200482 A1 | 7/2014 | Shi | |
| 2015/0042406 A1 | 2/2015 | Kovac et al. | |
| 2015/0133799 A1 | 5/2015 | O'Connell et al. | |
| 2015/0327836 A1 | 11/2015 | Stone et al. | |
| 2015/0342512 A1 | 12/2015 | Shi | |
| 2015/0366498 A1 | 12/2015 | Choi et al. | |
| 2016/0029912 A1 | 2/2016 | Stimpson | |
| 2016/0066831 A1 | 3/2016 | Hyde et al. | |
| 2016/0074581 A1 | 3/2016 | Gerrans | |
| 2016/0106323 A1 | 4/2016 | Ou et al. | |
| 2016/0183819 A1 | 6/2016 | Burnett et al. | |
| 2016/0331294 A1 | 11/2016 | Imran et al. | |
| 2016/0331451 A1 | 11/2016 | Nabutovsky et al. | |
| 2016/0354028 A1 | 12/2016 | Damaser et al. | |
| 2016/0374576 A1 | 12/2016 | Ziaie et al. | |
| 2017/0055874 A1 | 3/2017 | Papirov et al. | |
| 2017/0071566 A1 | 3/2017 | Hart et al. | |
| 2017/0100561 A1 | 4/2017 | Burnett | |
| 2017/0128012 A1 | 5/2017 | Parks et al. | |
| 2017/0136209 A1 | 5/2017 | Burnett et al. | |
| 2017/0156610 A1 | 6/2017 | Quackenbush et al. | |
| 2017/0156611 A1 | 6/2017 | Burnett et al. | |
| 2017/0160175 A1 | 6/2017 | Al-Mayah | |
| 2017/0258345 A1 | 9/2017 | Smith | |
| 2017/0259035 A1 | 9/2017 | Smith et al. | |
| 2017/0332955 A1 | 11/2017 | Burnett et al. | |
| 2018/0177458 A1 | 6/2018 | Burnett et al. | |
| 2018/0184929 A1 | 7/2018 | Burnett et al. | |
| 2018/0344184 A1 | 12/2018 | McKinney et al. | |
| 2018/0344234 A1 | 12/2018 | McKinney et al. | |
| 2018/0344250 A1 | 12/2018 | McKinney et al. | |
| 2019/0282109 A1 | 9/2019 | Schlumpf et al. | |

FOREIGN PATENT DOCUMENTS

| | | |
|---|---|---|
| EP | 0097454 A2 | 1/1984 |
| WO | WO 1995/012351 | 5/1995 |
| WO | WO 2005/013834 | 2/2005 |
| WO | WO 2006/060248 | 6/2006 |
| WO | WO 2011/053500 | 5/2011 |
| WO | WO 2012/006624 | 1/2012 |
| WO | WO 2014/160300 | 10/2014 |
| WO | WO 2014/210453 | 12/2014 |
| WO | WO 2015/191125 | 12/2015 |

(56) References Cited

FOREIGN PATENT DOCUMENTS

| WO | WO 2016/049654 | 3/2016 |
| WO | WO 2016/204631 | 12/2016 |
| WO | WO 2017/156451 | 9/2017 |
| WO | WO 2018/136306 | 7/2018 |

OTHER PUBLICATIONS

Wilmink FA, et al., "Fetal complications after placement of an intrauterine pressure catheter: a report of two cases and review of the literature". J Matem Fetal Neonate Med 2008;21:880-883.

Extended European Search Report dated Mar. 2, 2020 for European Application No. EP 19210264.8.

International search report and written opinion for international application PCT/US2018/028687 dated Sep. 28, 2018.

International search report and written opinion for international application PCT/US2018/028693 dated Sep. 28, 2018.

International search report for international application PCT/US2018/034781 dated Sep. 5, 2018.

International search report for international application PCT/US2018/032467 dated Sep. 5, 2018.

Iberti TJ, Lieber CE, Benjamin E., "Determination of Intra-abdominal Pressure Using a Transurethral Bladder Catheter: Clinical Validation of the Technique," Anesthesiology, Jan. 1989, 70(1), 47-50.

Sascha S., et al., "Pressure Measurement Techniques for Abdominal Hypertension: Conclusions from an Experimental Model", Crit Care Res Pract., May 2015: 278139.

Muller, M., et al., "A randomized comparison of microtip and air-charged catheter for the measurement of maximum urethral closure pressure", Ginekol Pol. 2012, 83: 586-589.

"Dystocia and Augmentation of Labor", ACOG practice bulletin No. 49 Washington, DC: American College of Obstetricians and Gynecologist, Dec. 2003: 1445-1454.

Bakker, J., et al, "Outcomes after internal verses External Tocodynamometry for Monitoring Labor", The N Engl J Med, 2010, 362:306-3013.

Euliano T., et al., "Monitoring uterine activity during labor: a comparison of 3 methods", Am J Obstet Gynecol. Jan. 2013; 208:66, 1-6.

Matsuo K, Lynch MA, Kopelman JN, Atlas RO. "Anaphylactoid syndrome of pregnancy immediately after intrauterine pressure catheter placement". Am J Obstet Gynecol 2008; 198: e8-e9.

D.J. Sawchuck, B.K. Wittmann "Pre-eclampsia renamed and reframed: Intra-abdominal hypertension in pregnancy", Medical Hypotheses 83 (2014) 619-632.

Madanes AE, David D, Cetrulo C. "Major complications associated with intrauterine pressure monitoring." Obstet Gynecol, 1982;59:389-391.

Sugerman HJ., "Hypothesis: Preeclampsia is a venous disease secondary to an increased intra-abdominal pressure", Medical Hypotheses: 77 (2011)841-849.

Brent K. Lind, MD "Complications caused by extramembranous placement of intrauterine pressure catheters", Am J Obstet Gynecol 1999;180:1034-1035.

(Abstract Only) Devoe, LD, et al. "Monitoring intrauterine pressure during active labor. A prospective comparison of two methods", J Reprod Med. Oct. 1989; 34(10): 811-814.

(Abstract Only) Wilmink FA, et al., "Fetal complications after placement of an intrauterine pressure catheter: a report of two cases and review of the literature". J Matern Fetal Neonate Med 2008;21:880-883.

Rood, Kara M., et al."Use of Intrauterine Pressure Catheters (IUPPC) Increases Risk of Post-Cesarean Surgical Site Infection", Obstetric & Gynecology: May 2017, 129: 22 S.

\* cited by examiner

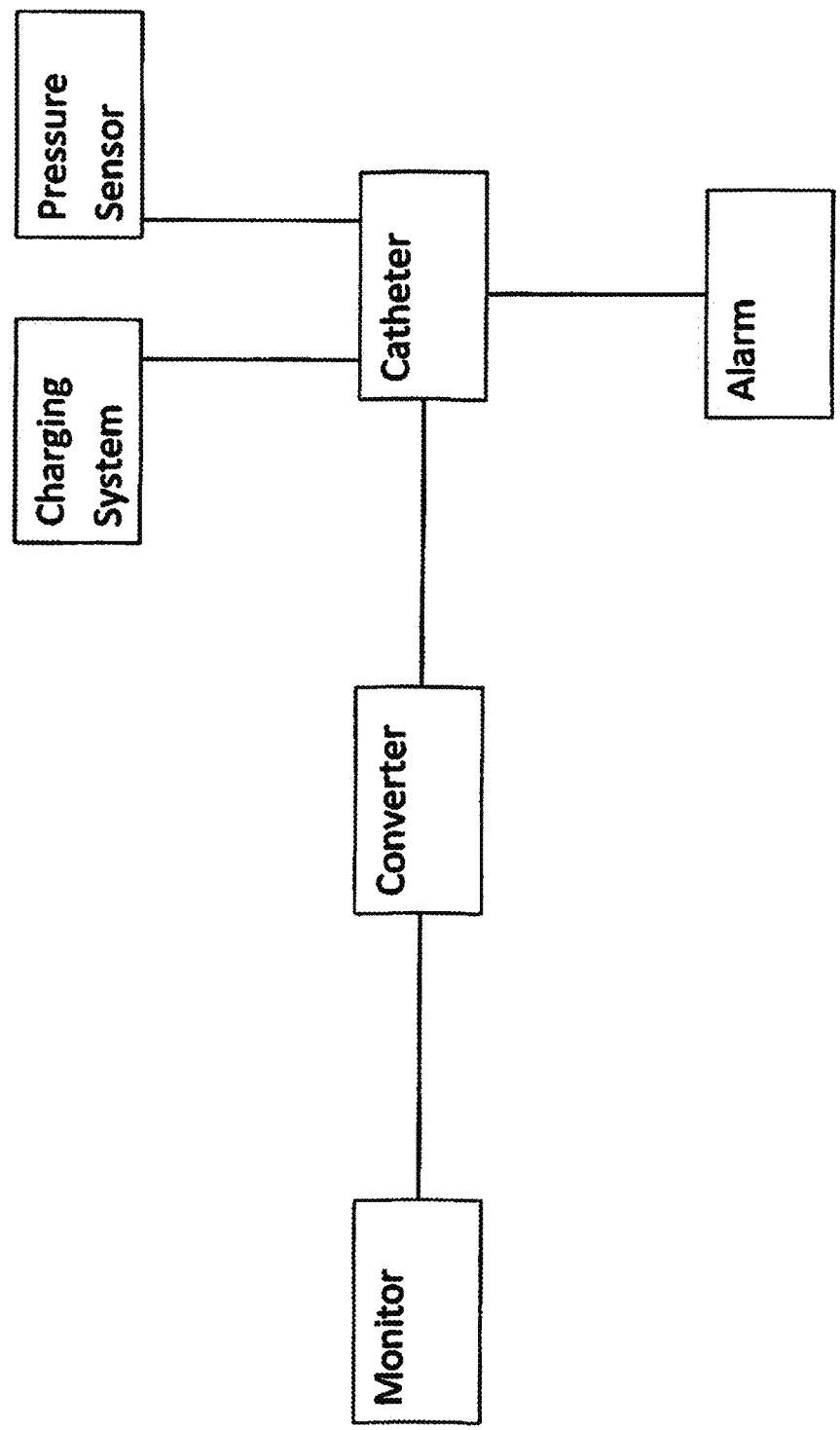

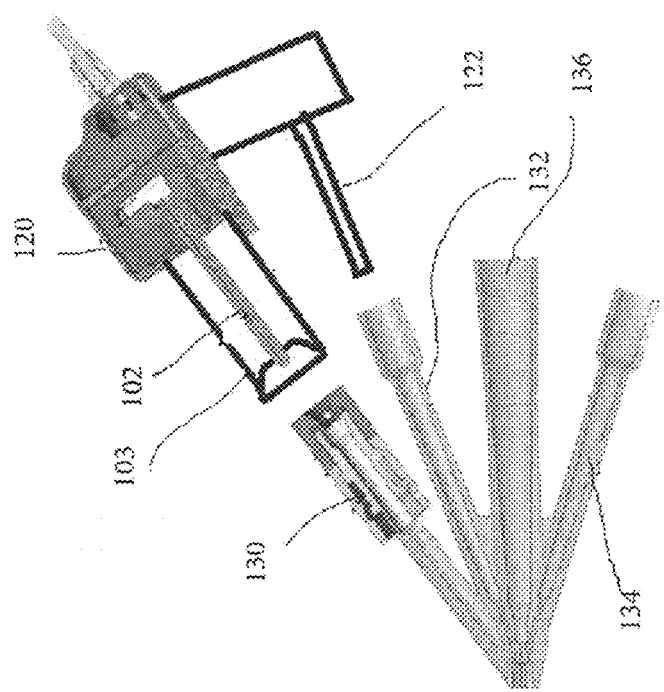

CATHETER FOR MONITORING INTRAUTERINE PRESSURE TO PROTECT THE FALLOPIAN TUBES

This application claims priority from provisional application Ser. No. 62/590,513, filed Nov. 24, 2017 and is a continuation in part of application Ser. No. 15/949,022, filed Apr. 20, 2018 which claims the benefit of provisional application Ser. No. 62/544,690, filed Aug. 11, 2017, provisional application Ser. No. 62/514,793, filed Jun. 3, 2017, provisional application Ser. No. 62/590,513, filed Nov. 24, 2017 and provisional application Ser. No. 62/622,871, filed Jan. 27, 2018. The entire contents of each of these applications are incorporated herein by reference.

BACKGROUND OF THE INVENTION

1. Field of the Invention

This application relates to a device and method for monitoring or measuring intrauterine pressure exerted in the fallopian tube during Hysterosalpingogram (HSG), Sonohysterogram (SHG), Hysterosalpingo-contrast sonography (HyCoSy) or Saline Infused Sonogram (SIS) so as to protect the fallopian tubes while determining patency.

2. Background

During Hysterosalpingogram (HSG), Sonohysterogram (SHG), Hysterosalpingo-contrast sonography (HyCoSy) or Saline Infused Sonogram (SIS) procedures unrecognized excess pressure in the uterine cavity can lead to extravasation of the dye or the fluid into the uterine vasculature. This unrecognized excess pressure can also damage the fallopian tubes.

A hysterosalpingogram or "HSG" is an X-ray procedure to examine the uterus and fallopian tubes via injection of a radiographic dye. It is a common diagnostic test performed during evaluation of female fertility. It is usually performed in the radiology department of a hospital or outpatient radiology facility, in which radiographic dye is injected into the uterus through the cervix. The uterus fills with dye which, if the fallopian tubes are open, fills the tubes and spills into the abdominal cavity. This shows whether the fallopian tubes are open or blocked, as well as the location of any blockage. The HSG, however, has a major shortcoming in that it is not data-driven. In a study of 325 infertile patients, researchers measured the pressure at which dye passed through the fallopian tubes ("tubal perfusion pressure") and found that the lower tubal perfusion pressure was correlated with a higher fertility rates, thereby suggesting the importance of improving clinical understanding of the relationship between tubal perfusion pressure and fertility. Existing HSG catheters, such as the Cooper Surgical HGS/HS catheter Set and the Utah Medical Trans-Vaginal Ultrasound HSG catheter, however, are merely conduits for the radiographic dye injected into the uterus. They do not provide information about the intra-uterine pressure as dye fills the uterine cavity. Moreover, since they provide no information regarding pressure generated during the procedure, the excess pressure can cause dye to get pushed into the fragile uterine vasculature especially if the fallopian tubes are blocked due to disease. If the fallopian tubes are noted to be patent during the procedure than it would be beneficial to know the pressure generated in the uterus during the process. As noted earlier, the lower pressure correlates with increased chance or spontaneous fertility when fallopian tubes are noted to be patent. All in all it is beneficial to know the intrauterine pressure generated during these procedures so as to protect the uterus and the fallopian tubes.

A sonohysterogram is an ultrasound exam in which fluid is put into the uterus through the cervix (like an HSG) and sound waves are used to create images of the uterine cavity and fluid spillage from the fallopian tube. Saline infused Sonogram (SIS) is a test where saline is inserted into the uterus, allowing the uterine lining (endometrium) or uterine cavity to be seen. Both of these procedures are a special kind of ultrasound exam in which fluid is put into the uterus and sound waves are used to create images of the uterine lining or the uterine cavity. The fluid helps show more detail than when ultrasound is used alone. Although HSG is still widely used as a first-line procedure for evaluating female infertility, ultrasound imaging advances have led to SIS and hysterosalpingo-contrast sonography (HyCoSy) replacing HSG in many centers around the world.

Determination of the tubal patency is essential for diagnosis of female infertility. In general, infertility is defined as not being able to get pregnant after one year of unprotected sex. According to the CDC, about 6% of US married women aged 15-44 years are unable to get pregnant after one year of trying; and about 12% of US women regardless of marital status aged 15-44 years have difficulty getting pregnant or carrying a pregnancy to term. It is estimated that in the U.S. alone over 480,000 women struggle to conceive each year.

Determination of the tubal patency is also required by the FDA after an Essure procedure for confirmation of tubal occlusion. There are various tubal occlusion procedures elected by a patient to prevent conception such as the Essure procedure in which a soft, flexible insert is placed into each fallopian tube, and a barrier subsequently forms around the inserts; or a surgical procedure in which the fallopian tubes are clamped and blocked, or severed and sealed, to prevent eggs from reaching the uterus.

Although the foregoing procedures/devices effectively image the flow of dye to determine whether the fallopian tubes are blocked or open, these procedures do not provide any way to protect the uterus or the fallopian tubes from damage during the procedure as described above. It would therefore be advantageous to provide a device which not only determines the tubal patency but also prevents exertion of excess force in the uterine cavity which may damage the fallopian tubes during the imaging procedure. Too much pressure could also blow open a tract in the occluded fallopian tubes leading to increased risk of ectopic pregnancy and or unwanted pregnancy. More importantly, it would be advantageous to know how much pressure is exerted in the uterus when the fluid runs through the fallopian tubes and noted to spill into the abdominal cavity.

SUMMARY

There are numerous procedures which utilize insertion of dye into the uterus and fallopian tubes and followed by imaging via X-ray or ultrasound. These procedures are used to diagnose infertility and to diagnose efficacy of the permanent birth control by determination if the fallopian tubes are patent. However, if the dye is injected, especially in a case where the fallopian tubes are not sufficiently open or are closed, excess pressure can be exerted on the fallopian tubes causing damage to the tubes and is seen readily by dye extravasating into the blood vessels around the uterus and the fallopian tubes. Excess pressure exerted during the procedure can also cause severe and prolonged pain due to the damaged tubes. The present invention provides a device to measure the intrauterine pressure in the uterus and the fallopian tubes during HSG, SHG, HyCoSy, or SIS procedures or other procedures. In addition the device can help protect and reduce the risk of harm to the uterus and the fallopian tubes. This is accomplished by an accurate pressure monitoring system which can determine the pressure within the uterus since closed fallopian tubes would cause unwanted pressure by the dye within the uterus. The present invention therefore overcomes the deficiencies and disadvantages of the prior art. The physician can accurately apply specific amount of pressure in the uterus to determine the opening pressure of the patent fallopian tubes and protect the uterus from unrecognized excess pressure generated when fallopian tubes are occluded.

The catheters of the present invention utilize an air-charged chamber or a micro-tip sensor to measure intrauterine pressure and enable pressure to be measured continuously if desired. Various types of sensors and different locations of the sensors are utilized with the several embodiments of the catheters of the present invention. Each of these various embodiments is discussed in detail herein.

Some embodiments of the catheter of the present invention include a blocking member to block the outflow of dye from the uterus. These embodiments are discussed in more detail below.

In accordance with one aspect of the present invention, a multi-lumen catheter for monitoring intrauterine pressure to prevent damage to the fallopian tubes is provided. The catheter comprises an elongated body configured and dimensioned for insertion into a uterus of a patient, the catheter having a first lumen, a second lumen, and a first balloon at a distal portion. The first lumen communicates with the first balloon, and the second lumen has an opening within the uterus for injection of dye or other fluid into the uterus. The first balloon contains a gas to form along with the first lumen a gas containing chamber to monitor pressure within the uterus to thereby prevent excessive pressure applied to the fallopian tubes of the patient. A sensor is in communication with the first lumen to measure pressure about a circumferential area of the first balloon to measure pressure, preferably continuously, of the uterus to provide readings of intrauterine pressure.

In accordance with another aspect of the present invention, a multi-lumen catheter for monitoring intra uterine pressure to prevent damage to the fallopian tubes of a patient is provided. The catheter comprises an elongated body configured and dimensioned for insertion into a uterus of a patient, the catheter having a first lumen, a second lumen and a pressure sensor. The pressure sensor is positioned within a distal region of the first lumen, the second lumen having an opening within the uterus for injection of dye or other fluid into the uterus, and the sensor monitoring pressure within the uterus to thereby ensure pressure in the fallopian tubes of the patient does not exceed a predetermined pressure.

In accordance with another aspect of the present invention, a multi-lumen catheter for monitoring intrauterine pressure to prevent damage to fallopian tubes of a patient is provided. The catheter is configured and dimensioned for insertion into a uterus of a patient. The catheter comprises a first lumen, a second lumen, an expandable outer balloon at a distal portion and an expandable inner balloon within the outer balloon, the first lumen communicating with the inner balloon and the second lumen communicating with the uterus to inject dye or other fluid into the uterus for imaging. The inner balloon and first lumen contain a gas to form a gas containing chamber to monitor pressure within the uterus to determine if pressure exceeds a threshold pressure which could damage the fallopian tubes of the patient. The outer balloon has a circumferential area greater than a circumferential area of the inner balloon, wherein in response to pressure within the uterus exerted on an outer wall of the outer balloon, the outer balloon deforms and exerts a pressure on an outer wall of the inner balloon to deform the inner balloon and compress the gas within the inner balloon and the first lumen to provide a finer measurement, the pressure sensor measuring intrauterine pressure based on gas compression caused by deformation of the inner balloon.

In accordance with another aspect of the present invention, a method for determining a condition of fallopian tubes and for measuring intrauterine pressure is provided comprising the steps of:

providing a catheter having first and second lumens and an expandable first balloon in communication with the first lumen, inserting the catheter into a uterus of a patient;

connecting a hub containing a pressure transducer to the first lumen to automatically advance air through the first lumen of the catheter to expand the first balloon to a more expanded condition;

injecting dye or other fluid through the second lumen into the uterus to assess an open or closed condition of the fallopian tubes;

obtaining a first pressure reading of the uterus based on deformation of the first balloon in response to pressure exerted on the first balloon; and transmitting the first pressure reading to an external monitor connected to the hub to indicate pressure, the indicated pressure indicative of pressure exceeding a threshold pressure which could damage the fallopian tubes.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 3 is a schematic view of the system utilizing the catheter of FIG. 1A with an alarm system;

FIG. 12 is a schematic view of an alternate embodiment of the pressure transducer hub connectable to two side ports of the catheter;

DETAILED DESCRIPTION OF PREFERRED EMBODIMENTS

Figure 1A:
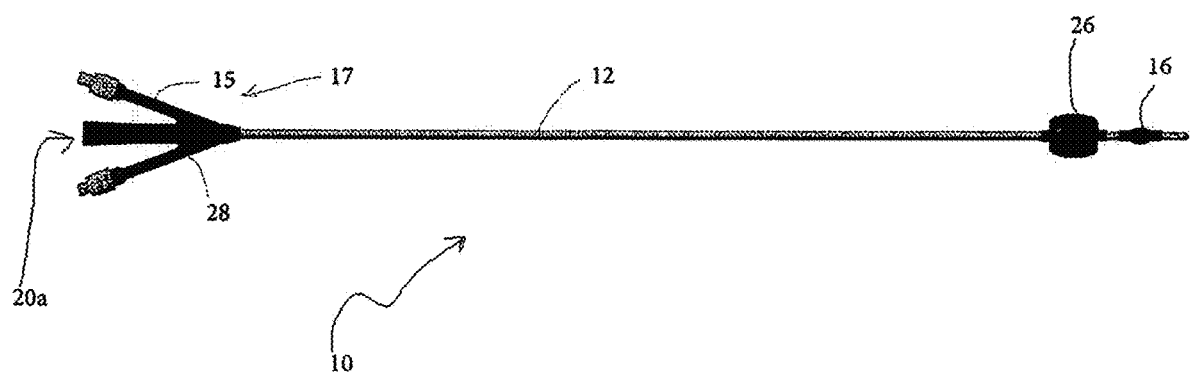
FIG. 1A is a side view of a first embodiment of the catheter of the present invention having a pressure sensing balloon, the balloon shown in the inflated (expanded) condition.

The catheters of the present invention are designed to determine the condition of the fallopian tubes, i.e., whether the fallopian tubes are open or closed, in fertility and/or infertility procedures via dye injection while protecting the fallopian tubes to prevent damage to the fallopian tubes. More specifically, the catheters of the present invention are inserted through the vagina and cervix and into the uterus and enable a) injection of dye for imaging of the fallopian tubes via X-ray, ultrasound or other methods; and b) continuously, safely, and accurately measure intra-uterine pressure to ensure excess pressure is not exerted on the fallopian tubes and/or the uterine muscle from the dye injection. More specifically, if the dye is injected, especially in a case where the fallopian tubes are not sufficiently open or are closed, excess pressure can be exerted on the fallopian tubes causing damage to the tubes. Excess pressure could also be exerted on the uterus. Thus, the catheters of the present invention measure intrauterine pressure as the dye fills the uterine cavity and monitor the pressure: decreasing or plateauing intra-uterine pressure signifies the fallopian tubes are open; non-plateauing of intrauterine pressure signifies the fallopian tubes are blocked and that too much pressure may be exerted by the dye on the fallopian tubes and/or the uterine muscle. If too much pressure is exerted, it may be accompanied by visual presentation of dye being pushed into the tubal blood vessels or uterine muscle, causing extravasation of the x-ray dye or fluid leading to possible damage/allergic/anaphylaxis within the patient. Thus, the present invention provides a device/system and method to protect and reduce the risk of harm to the fallopian tubes and uterus while performing the diagnostic procedure. In preferred embodiments, constant monitoring of pressure is provided so critical time periods are not missed.

The present invention provides a multi-lumen catheter insertable through the vagina and cervix into the uterus in the same manner as a HSG catheter. The catheters of the present invention utilize in some embodiments a gas (e.g., an air) charged chamber to measure uterine pressure across a large surface area. In other embodiments, the catheters of the present invention utilize a microtip pressure sensor at a distal end of the catheter to measure uterine pressure. In either case, the sensor provides the doctor with real-time information on 1) increasing intra-uterine pressure as dye or fluid fills the uterine cavity; 2) decreasing or plateauing intra-uterine pressure; and/or 3) non-plateauing of intra-uterine pressure if the fallopian tubes are blocked. The pressure measurement can also assist physicians in determining the normal opening pressure for the fallopian tubes.

The catheters of the present invention have a lumen to inject radiographic dye into the uterus for flow into the fallopian tubes to assess blockage of the fallopian tubes and a lumen for measuring intra-uterine pressure to assure the fallopian tubes are not damaged. In some embodiments, the catheter can have a third lumen for inflation of a retention (stabilizing) and sealing balloon to block outflow of dye; in other embodiments the catheter has a sealing member, e.g., a stopper or cork, stationary or slidable on the catheter shaft, to block outflow of dye and stabilize the thin flexible catheter to better enable insertion into the uterine cavity. Each of these embodiments is discussed in detail below.

Referring now to the drawings and particular embodiments of the present invention wherein like reference numerals identify similar structural features of the devices disclosed herein, there is illustrated in FIG. 1 a catheter of a first embodiment of the present invention. The catheter (device) is designated generally by reference numeral 10 and is configured for insertion into and positioning within the uterus of the patient for injecting radiographic dye and measuring intrauterine pressure. The catheter can be connected to a handheld or bedside or central monitor through a wire (or cable) or blue tooth wireless connection to display continuous readings of the measured pressure. Opening pressure of the fallopian tubes could also be measured.

Turning now to details of the catheter 10, which is also referred to herein as the device 10, and with initial reference to FIGS. 1A-2B, the three-lumen catheter 10 has an elongated flexible shaft 12 having a lumen (channel) 14 extending within the shaft 12 and communicating at its distal region with balloon 16 to fluidly communicate with balloon 16 to inflate the balloon. Balloon 16 is utilized for monitoring pressure and is sometimes referred to herein as the "pressure balloon." A fluid side port 15 is positioned at a proximal region 17 of the catheter 10 for communication with an infusion source for infusion of gas, e.g., air, through the lumen 14 and into the balloon 16. The catheter 10 is shown in FIG. 1 with balloon 16 in the inflated condition (position) for positioning within the uterus. It is inserted into the uterus in the deflated (collapsed) condition.

The shaft 12 also includes a second lumen (channel) 24 with a proximal opening 20a and a third lumen (channel) 24 extending therein. The second lumen 24 is configured for insertion of radiographic dye for flow into the uterus and fallopian tubes. The second lumen can have a distal opening and/or a side opening 20b at a distal portion, communicating with the uterus. The side opening 20b is shown distal of the balloon 16; in alternate embodiments, the side opening can be proximal of the balloon 16. The third lumen 24 terminates at its distal end within balloon 26 to fluidly communicate with balloon 26 to inflate the balloon 26. The balloon 26 is inflatable to stabilize/retain the catheter 10 to limit movement of the catheter 10 to keep it in place and is sometimes referred to herein as "the stabilizing balloon" or "retention balloon." The retention balloon is preferably sized to block the outflow of dye from the uterus and can therefore also function as a sealing balloon. Alternatively, a separate sealing balloon or sealing member could be provided in addition to the stabilizing balloon. A fluid side port 28 is positioned at the proximal region 17 of the catheter 10 for communication with an infusion source for infusion of fluid through the lumen 24 and into the stabilizing balloon 26. The balloon can be filled with fluid, e.g., liquid such as water or saline, or a gas, e.g., air. In FIG. 1A, the balloon 26 is shown in the inflated condition and is in the deflated (collapsed) condition during insertion of the catheter.

FIG. 1 is a transverse cross-section of the catheter showing the three lumens. The cross-sectional shapes and sizes of the lumens in the drawings are provided by way of example as one or more of the lumens of the various catheter embodiments disclosed herein (including FIG. 1A) can be other shapes, e.g., circular, oval or other symmetrical or asymmetrical shapes in transverse cross section. This also applies to the cross-sectional configurations of the lumens of the other embodiments herein.

A sensor 30 is positioned within lumen 14 adjacent balloon 16. The wire(s) 32 are shown extending through lumen 14, the sensor 30 and wire(s) 32 being of sufficiently small size so as not to interfere with gas, e.g., air, flow though lumen 14. The sensor 30 measures intrauterine pressure. The sensor 30 is part of a transducer for converting the variation in pressure to an electrical signal for transmission to an external monitor. The transducer can be wired directly to the monitor or alternatively wired to a converter external of the catheter for converting the signal received by the transducer and transmitting a signal to the monitor, e.g., a bedside monitor, to display the pressure readings. This is shown schematically in FIG. 3. The readings can be displayed in quantitative form, graphical form or other displays to provide an indicator to the clinician of the intrauterine pressure. Alternatively, the sensor/transducer can be connected to the monitor via a Bluetooth wireless connection.

Wires 32 can extend though lumen 14 and exit side port 15 for connection to a converter or monitor or alternatively can be inserted through the lumen 14, piercing the wall to enter the lumen 14 distal of the side port.

An indicator or alarm system can also be provided wherein the system includes a comparator for comparing the measured pressure to a threshold (predetermined) value, and if such threshold is exceeded, an indicator, e.g., an alarm, is triggered to indicate to the clinician the excessive pressure. An alarm system can alternatively or in addition be activated if a change in pressure measurement exceeds a specified rate over a specified period of time. This would alert the staff to an imminent risk of pressure exceeding a certain threshold or predetermined value (pressure). The indicator or alarm can be on (part of) the catheter or alternatively on an external device such as the monitor. The alarm can also be connected via wireless connection to a phone or remote device to alert the appropriate personnel. Such indicator or alarm system can be utilized with the other embodiments disclosed herein. In embodiments wherein other parameters are measured, the alarm system described herein can be tied into measurement of these parameters.

The lumen 14 and space within balloon 16 together form a closed gas, e.g., air chamber, i.e., the lumen 14 forming a gas column. With the balloon 16 filled with air (or other gas), pressure on the external wall of the balloon 16 will force the balloon to deform inwardly, thereby compressing the air contained within the balloon space and within the lumen 14. The pressure sensor 30 is located in a distal portion of the lumen 14 at the region of the balloon 16 and thus is positioned at the distal end of the air column. Therefore, the pressure is sensed at the distal region as the sensor 30 detects change in gas pressure in lumen 14 due to balloon deformation. Placement of the sensor 30 at a distal location provides a pressure reading closer to the source which in some applications can increase the accuracy by reducing the risk of transmission issues by reducing the amount of interference which could occur due to water, air, clots, tissue, etc. if the transmission is down the air lumen (air column).

Additionally, the pressure measurement occurs about a more circumferential area of the balloon 16 providing a pressure reading of a region greater than a point pressure sensor reading. Also, average pressure over an area of the uterine wall can be computed. Thus, the area reading gleans information on pressure over more of the uterine wall. Stated another way, the balloon has a relatively large surface area with multiple reference points to contribute to average pressure readings of the surface around it.

The air column is charged by insertion of air through the side port 15 which communicates with lumen 14. The side port 15 includes a valve to provide a seal to prevent escape of air from a proximal end. The balloon 16 can be composed of impermeable material, or in alternative embodiments, a permeable or semi-permeable material with an impermeable coating. This seals the air column at the distal end to prevent escape of air through the distal end, i.e., through the wall of the balloon 16. Thus, with the lumen sealed at the proximal end and the balloon sealed at the distal end, a closed air (or other gas) system (air charged system) is provided.

In preferred embodiments, when the lumen 14 is air charged, the balloon 16 is not fully inflated. This improves the accuracy of the balloon 16 transmitting pressure from external the balloon to the interior of the balloon and into the lumen, i.e., air column, by ensuring the balloon has sufficient compliancy to prevent the balloon from introducing artifact into the pressure reading which would diminish its accuracy. That is, in preferred embodiments, the pressure balloon 16 is not fully inflated so it would receive less than the maximum volume. Thus, with a balloon of maximum x volume, the balloon would receive X-Y fluid, with Y representing the amount of desired extra space to achieve desired compliancy of the balloon while still enabling sufficient inflation of the balloon to achieve its pressure induced deformation function. Thus, the use herein of gas or air filled chamber or balloon or lumen filled with gas encompasses the balloon completely filled or partially filled. The term gas containing chamber is therefore also used herein.

Note in this embodiment, the stabilizing balloon 26, also referred to as the proximal retention balloon, is positioned proximal of the pressure balloon 16. Also, in this embodiment, the stabilizing balloon 26 is larger than the pressure balloon 16. Alternatively, the stabilizing balloon can be smaller than the pressure balloon. Various shapes of the balloons are also contemplated.

It should be appreciated that although the stabilizing balloon is shown in the embodiment of FIG. 1, it is also contemplated as an alternative, the catheter and system of FIG. 1 can be utilized without the stabilizing balloon. Similarly, the various embodiments (catheter) disclosed herein could not include a stabilizing balloon or include a stabilizing balloon. Also, it is contemplated that instead of a stabilizing balloon another blocking member could be utilized as discussed below.

Figure 1B:
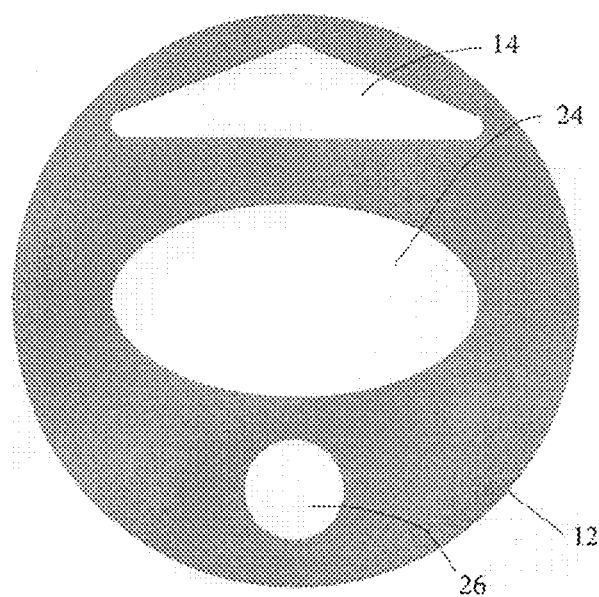
FIG. 1B is a transverse cross-sectional view of the catheter of FIG. 1A.
Figure 2A:
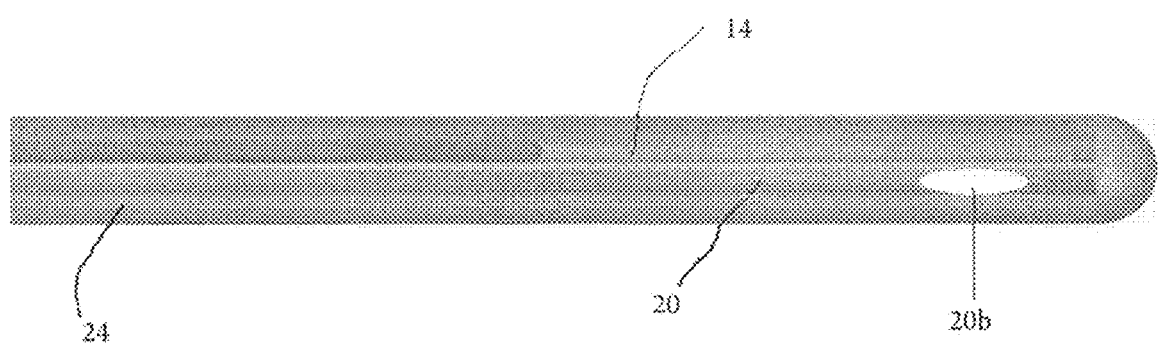
FIGS. 2A and 2B are close up views of the catheter of FIG. 1A.
Figure 2B:
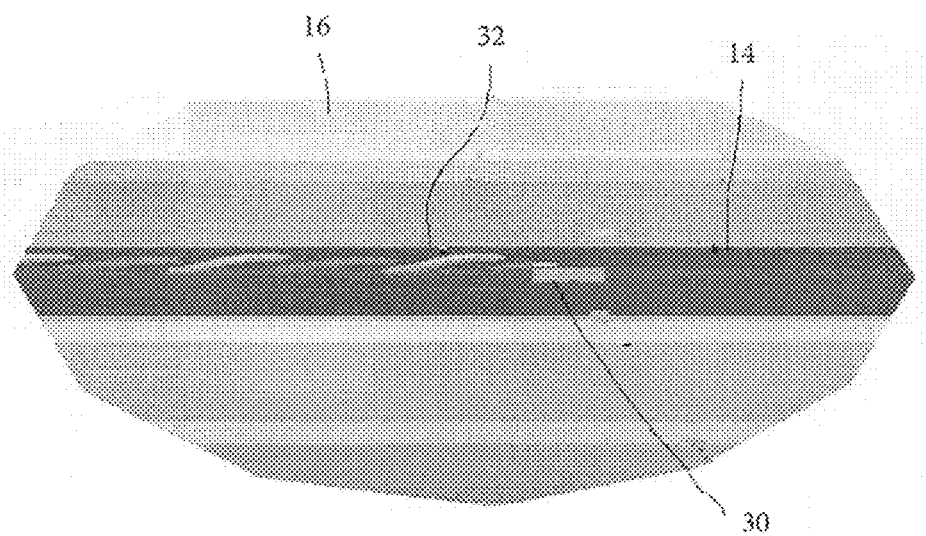
Figure 4A:
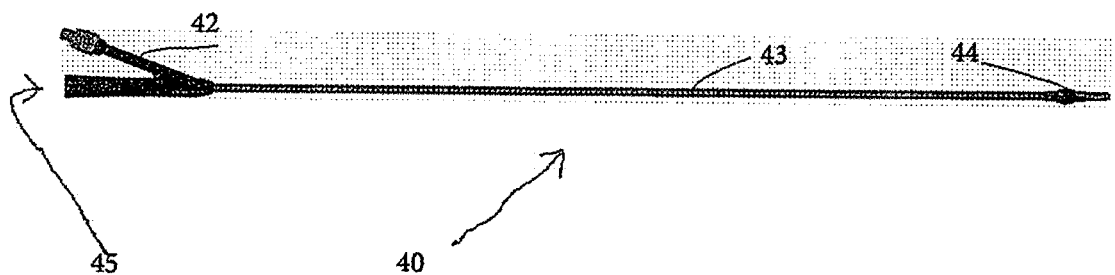
FIG. 4A is a side view of an alternate embodiment of the catheter of the present invention.
Figure 4B:
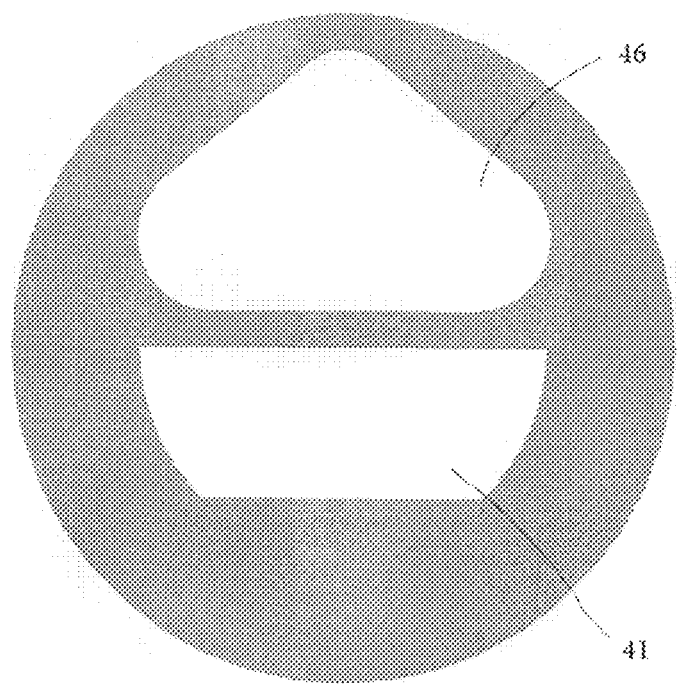
FIG. 4B is a transverse cross-sectional view of the catheter of FIG. 4A.
Figure 4C:
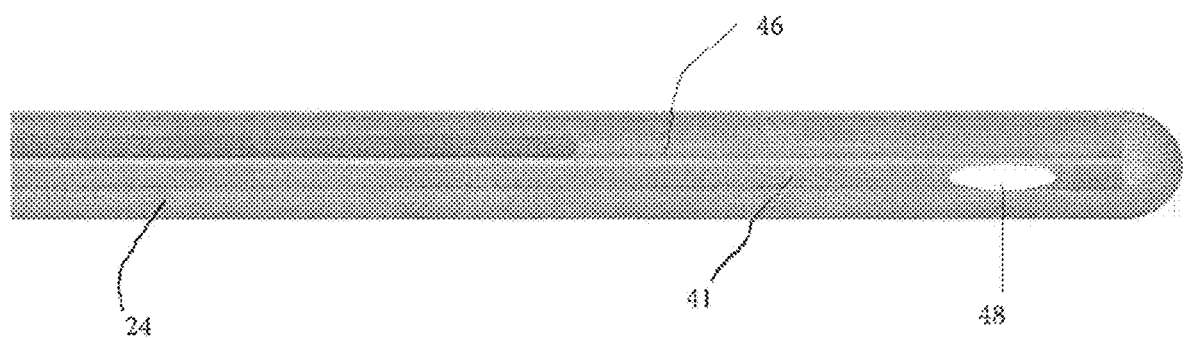
FIG. 4C is a close-up view of the sensor of the catheter of FIG. 4A.
Figure 7A:
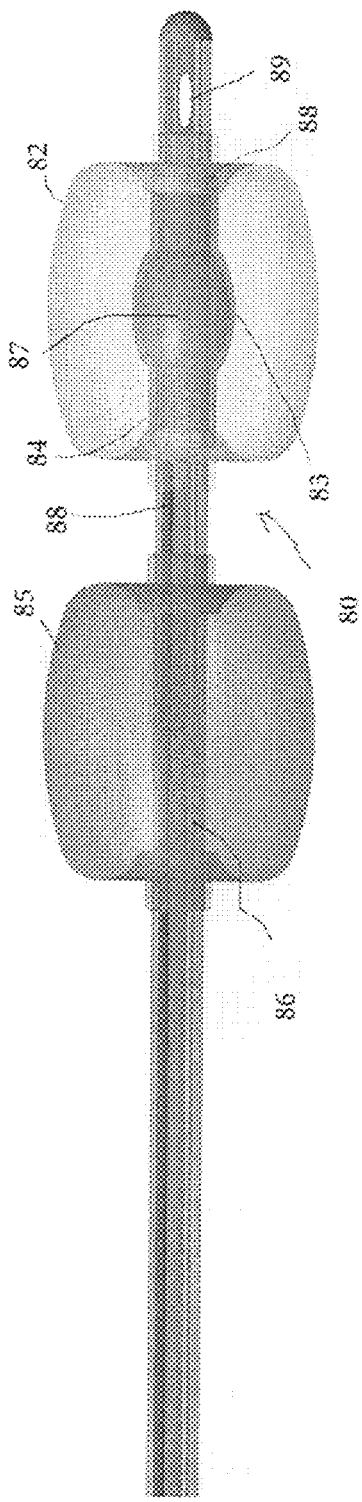
FIG. 7A is a side view of the distal region of a catheter of an alternate embodiment of the present invention having an outer and inner pressure balloon and a retention balloon, the balloons shown in the inflated condition.
Figure 7B:
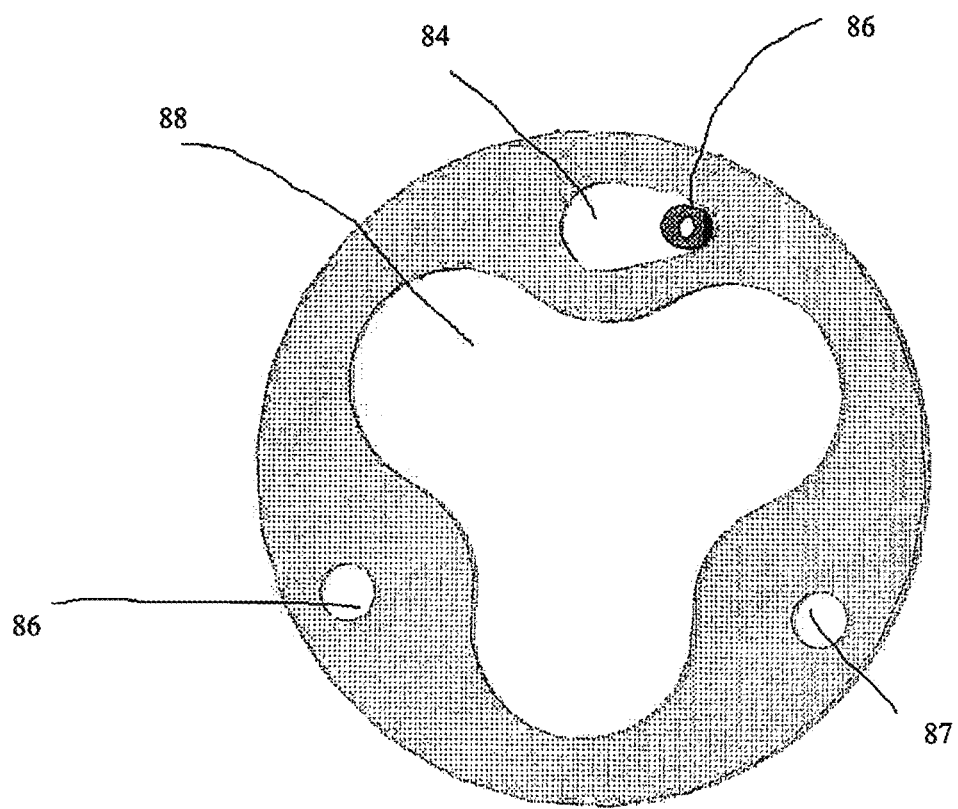
FIG. 7B is a transverse cross-sectional view of the catheter of FIG. 7A.

In the embodiment of FIGS. 4A-4C, catheter 40 has two lumens: 1) a lumen 41 for injection of radiographic dye which has a proximal opening 45 and a distal opening 48 to communicate with the uterus (similar to lumen 20 of FIG. 1); and 2) an air (or other gas) lumen 46 filling pressure balloon 44 (positioned at the distal end of shaft 43) via insertion of air (or other gas) through side port 42. The cross-sectional configuration of the lumens shown in FIG. 1B (and in FIG. 7B discussed below) are just two examples of the configuration as different sizes and shapes are also contemplated, e.g., circular, oval, symmetric, asymmetric, etc. The sensor is positioned within the air lumen in the same manner as sensor 30 is in lumen 14 or in the alternative positions disclosed herein. Thus, the pressure sensing described in conjunction with FIG. 1 is fully applicable to the embodiment of FIG. 4A. Besides the elimination of the stabilizing balloon and its lumen and side port, catheter 40 is the same as catheter 10. Catheter 40 can in some embodiments have a plug such as plug 47 of catheter 40' of FIG. 5A. Except for the plug 47, the catheter 40' is identical to catheter 40 and corresponding parts/components have been labeled with prime reference numerals. The plug can be located outside the cervix in the vagina to block outflow of dye. In the embodiment of FIG. 5B a sealing plug and a retention balloon are provided. More specifically, catheter 50 of FIG. 5B has a pliable outer sheath 52 slidable over the catheter. The sheath 52 can provide additional stability to the catheter. A tab 53 extending from the sheath 52 at a proximal end can be provided to assist sliding of the sheath 52 in proximal and distal directions, although other types of handles or grips can be provided to facilitate sheath sliding. A sealing plug 54 extends from the sheath 52 at a distal end and can be conically shaped as shown, although other shapes are contemplated, to help seal the cervical os. A retention balloon 56 is positioned in the uterus to help retain the catheter 50, and in some embodiments can perform an additional sealing function. The distal tip 51 of the catheter 50 has a side opening 53 for injecting fluid. The catheter 50 includes a sensor (not shown) such as a microtip sensor, a pressure balloon or any of the sensors disclosed herein. Note the sliding sheath with seal can be utilized with any of the embodiments described herein.

Note that although only one sensor is shown in FIGS. 1 (and 4), it is also contemplated that multiple sensors can be provided. Also, note that the sensor 30 is positioned in lumen 14 at a mid-portion of the balloon, i.e., just proximal where the opening in lumen 14 communicates with the interior of the balloon 16. It is also contemplated that the sensor can be placed at another portion within the lumen 14, e.g., a more proximal portion, with respect to the lumen opening. Also, the lumen opening need not be at the mid portion of the balloon and can be at other regions of the balloon to communicate with the interior space of the balloon. Note if multiple sensors are provided, they can be positioned at various locations within the lumen 14.

As shown, the sensor 30 and its transmission wires are located in the same lumen 14 also used for inflation fluid, e.g., a liquid or a gas such as air, for balloon 16 (or 44) and for the gas, e.g., air charged column. This minimizes the overall transverse cross-section (e.g., diameter) of the catheter 10 by minimizing the number of lumens since additional lumens require additional wall space of the catheter. However, it is also contemplated in alternate embodiments that the sensor is located in a dedicated lumen separate from the pressure balloon inflation lumen. This can be useful if a larger sensor or additional wires are utilized which would restrict the air lumen if provided therein. This is also useful if a specific sized lumen for the sensor and wires is desired to be different than the sized lumen for the air column. Thus, in this embodiment, the catheter would have the following lumens: 1) a lumen for injection of dye to communicate with the uterus (similar to lumen 20 of FIG. 1); 2) a lumen for filling the pressure balloon; and 3) a lumen in which the sensor (similar to sensor 30) and its transmission wires (similar to wires 32) are contained; and if the catheter includes a retention balloon, a fourth lumen for filling the retention balloon.

Turning now to the use of the catheter 10, the catheter 10 is inserted through the vagina and cervix into the uterus. Note the other catheters (e.g., catheter 40 and 40') would be used in the same manner. The balloon 26 is inflated to secure the catheter 10 in place during the procedure by insertion of a fluid (liquid or gas) through side port 28 which is in fluid communication with lumen 24. The inflated balloon 26 also blocks the outflow of dye. The system is charged by inflation of the balloon 16, i.e., preferably partial inflation for the reasons discussed above, by insertion of air (or other gas) via a syringe or other inflation device through port 15 which is in fluid communication with lumen 14. As discussed above, the catheter 10 is a closed system with the balloon 16 sealed so that air (or other gas) inserted through lumen 14 and into balloon 16 cannot escape through balloon 16. Thus, a closed chamber is formed comprising the internal space of the balloon 16 and the internal lumen 14 communicating with the internal space. With the balloon 16 inflated, dye is injected through the lumen 20 exiting opening 20b and pressure monitoring commences. When external pressure is applied to an outer surface of the balloon 16, caused by outward uterine pressure against the wall of balloon 16 due to the presence of dye, the gas within the chamber is compressed. The sensor 30 at the distal end of lumen 14 provides continuous pressure readings, converted to an electrical signal by the transducer within the distal end of lumen 14, and then electrically communicates through wire(s) 32 extending through lumen 14, exiting through the proximal side port 15 and connected to an external monitor. This enables determination of the pressure inside the uterus to ensure it does not reach a level (a predetermined level or threshold) where it could damage the uterus or the fallopian tubes into which the dye flows. Note the wire(s) can terminate at the proximal end in a plug in connector which can be connected directly to the monitor or alternatively plugged into a converter to convert the signals from the transducer in the embodiments wherein the converter is interposed between the wires and monitor (see e.g., the system of FIG. 3) to provide the aforedescribed graphic display. Although, the system is capable of continuous pressure monitoring, it can also be adapted if desired for periodic monitoring so the pressure readings can be taken at intervals or on demand by the clinician.

In the embodiments wherein an indicator is provided, if the measured pressure exceeds a threshold value, and/or a change in pressure measurement exceeds a specific rate over a specific time period, the indicator would alert the clinician, e.g., via a visual indication or an audible indication, that the threshold is exceeded. The indicator in some embodiments can include an audible or visual alarm (shown schematically in FIG. 3). In the embodiments having an indicator, the indicator can be provided on a proximal end of the catheter which extends out of the patient or the indicator can be part of an external component such as the monitor or a separate alarm system. A visual, audible, or other indicator can likewise be provided in any of the other embodiments disclosed herein to indicate if the measured pressure exceeds a predetermined value, and such indicator can include an alarm and can be part of the catheter or a separate component.

Figure 6:
FIG. 6 is a side view of an alternate embodiment of the present invention having an external transducer.

In the alternate embodiment of FIG. 6, catheter 60 is identical to the catheter 10 of FIG. 1A except that the pressure transducer is positioned external of the catheter rather than in the air lumen. That is, instead of the pressure transducer including the sensor being positioned within the distal end of the air lumen, the pressure sensor is positioned within a lumen at the distal end of the lumen and transmission wire(s) connect the sensor to the pressure transducer 64 positioned outside of the patient at a proximal region 61 of catheter 60. As shown, the pressure transducer 64 can be positioned in a side port 65 of catheter 60. In alternate embodiments, it is positioned outside the catheter. In all other respects, catheter 60 is identical to catheter 10 and therefore for brevity further discussion is not provided since the structure and function of the pressure and stabilizing balloon(s) 62, 63, plug (if provided), the lumens within shaft 66, the positioning of the sensors in the lumens, the continuous pressure monitoring, etc., as well as the aforedescribed alternative arrangements of catheter 10, are fully applicable to the catheter 60.

In an alternate embodiment, the catheter is identical to catheter 60 except that both the pressure transducer and the pressure sensor are positioned external of the patient at a proximal region of the catheter rather than in the air lumen. That is, instead of the pressure sensor being positioned within and at the distal end of the air lumen, the transducer and pressure sensor are positioned in a side port (like side port 65). In yet other embodiments, the pressure sensor and/or pressure transducer can be positioned within the air lumen at a proximal end of the air lumen. In either system, the system is charged by inflation of the balloon, i.e., preferably partially inflated for the reasons discussed above, by insertion of air (or other gas) via a syringe through the side port which is in fluid communication with the air lumen. The catheters like the aforementioned catheters are closed systems with the balloon sealed so that air inserted through lumen and into the balloon cannot escape through the balloon—a closed chamber is formed comprising the internal space of the balloon and the internal lumen communicating with the internal space of the balloon. Pressure applied against the balloon wall compresses the balloon and the gas within the chamber of the balloon, compressing the gas within the lumen creating a gas. e.g., air charged column along the lumen, with the sensor at the proximal end of the catheter measuring pressure of the gas column to provide continuous pressure readings, converted to an electrical signal by the transducer at the proximal end or external of the catheter, and then electrically communicates through wire(s) to an external monitor. The balloon, like balloon 16 and the other pressure balloons described herein, is of sufficiently large size to provide a sufficient circumferential area for detection of pressure changes along several parts of the uterine wall, thereby providing an average pressure and enabling more accurate pressure readings. Note the wires of the sensor can terminate at the proximal end in a plug in connector which can be connected directly to the monitor or alternatively plugged into a converter to convert the signals from the transducer in the embodiments wherein the converter is interposed between the wires and monitor to provide the aforedescribed graphic display. Although, the system is capable of continuous pressure monitoring, it can also be adapted if desired for periodic monitoring so the pressure readings can be taken at intervals or on demand by the clinician.

In an alternate embodiment, the catheter can include a pressure sensor within the balloon. That is, the pressure sensor is carried by the catheter and positioned within the balloon to measure pressure in response to deformation of the balloon in response to pressure exerted on an outer wall of the balloon due to intrauterine pressure. The pressure transducer can include a sensor or can be a separate component positioned at a proximal end of the catheter or external of the catheter As discussed above, the pressure balloon has a large circumferential area (and large volume) to provide multiple reference points for pressure readings and to provide an average pressure to enable more accurate readings. Thus, the pressure balloon provides for gross measurement.

In an alternate embodiment shown in FIG. 7, the pressure balloon for detecting pressure, designated by reference numeral 82, forms an outer balloon of catheter 80. Contained within the outer balloon 82 is an inner balloon 83. The inner balloon 83 provides a smaller diameter balloon and a smaller circumference (and volume) than the outer balloon 82. The inner balloon 83 together with the lumen 84 forms a smaller air column than in the embodiments discussed above where the larger balloon internal space communicates directly with the air lumen. This provides finer measurements. Thus, the compliant outer balloon 82 compresses the compliant inner balloon 83 which compresses the air within air lumen 84. The closed system is thereby formed by the internal space of the inner balloon 83 and the lumen 84. In certain instances, the smaller balloon air column can provide a more accurate reading from the average pressure determined by the larger outer balloon 82.

The inner balloon 83 and outer balloon 82 can be separately/independently inflated and closed with respect to each other so there is no communication, e.g., passage, of gas or liquid, between the inner and outer balloons 83, 82. The outer balloon can be filled with a gas or liquid such as saline.

The proximal and distal end of the inner balloon 83 in the illustrated embodiment are within the confines of the outer balloon 82, i.e., the proximal end of the inner balloon 83 is distal of the proximal end of the outer balloon 82 and the distal end of the inner balloon 83 is proximal of the distal end of the outer balloon 82. Thus, the inner balloon 83 is fully encapsulated within the outer balloon 82.

With this inner/outer balloon arrangement, the larger outer surface of the outer balloon 82 takes gross measurements and then the forces are concentrated on the smaller inner balloon to amplify/concentrate pressure on the small area of the inner balloon so small changes can be detected and waves transmitted to the pressure transducer (via the length of the lumen to a proximal transducer, e.g. an external pressure).

The pressure transducer and pressure sensor can be positioned within the lumen 84 in the same manner as sensor 30 of FIG. 1 and can function in the same manner. Alternatively, the pressure transducer can be at a proximal end of the catheter 80 as in the embodiment of FIG. 6 or external of the catheter. The transmission wires of the pressure sensor extend through lumen 84.

The catheter 80 can optionally include a stabilizing (retention) balloon 85 similar to balloon 26 of FIG. 1 which can also in some embodiments block proximal flow of the imaging dye. The catheter 80 would have a lumen, e.g., lumen 86, to inflate the stabilizing balloon 85. Alternatively, the catheter 80 can have a plug such as plug 47 of FIG. 5A which would block outflow of the dye, and in some embodiments, the plug can be slidable along the exterior of the catheter 80. Lumen 88 with side opening 89 (or a distal opening) provides for outflow of radiographic dye for imaging. Lumen 84 which is used to inflate the inner balloon 83 and create the gas column has an opening at a distal region to communicate with inner balloon 83. A separate lumen 87 has an opening at a distal region to communicate with the outer balloon 82 to fill the outer balloon 82.

In use, catheter 80 is inserted into the uterus and stabilizing balloon 85 is inflated to secure the catheter 80 in place and either blocks outflow of dye or a plug is slid distally into positon to block outflow of dye or a stationary plug is provided to block such outflow.) The system is charged by inflation of the inner balloon 83, preferably partially inflated for the reasons discussed above, by insertion of air through a side port which is in fluid communication with lumen 84 in a closed system formed by the internal space of the inner balloon 83 and the internal lumen 84 communicating with the internal space of inner balloon 83. Outer balloon 82 is filled, preferably partially inflated for the reasons discussed above, via injection of gas, e.g., air, or fluid, e.g., saline, through a separate lumen. With the outer balloon 82 inflated, pressure monitoring can commence as external pressure applied to the larger circumferential outer surface of the outer balloon 82 compresses and deforms the outer balloon 82 which compresses the inner balloon 83. As the inner balloon 83 is compressed and deformed in response to compression/deformation of the outer balloon 82 based on changes to uterine pressure resulting from dye injection, the sensor at the distal end of lumen 84 provides continuous pressure readings, converted to an electrical signal by the transducer within the distal end of lumen 84, and then electrically communicates through wires 88 extending through lumen 84 to an external monitor either directly or via a converter. Although, the system is capable of continuous pressure monitoring, it can also be adapted if desired for periodic monitoring so the pressure readings can be taken at intervals or on demand by the clinician.

Note that although separate lumens are provided for the inflation of inner balloon 83 and outer balloon 82, in an alternate embodiment, a single lumen can be utilized to inflate both balloons 83 and 82. In such embodiment, the catheter can have one less angled port and one less lumen since inflation of the outer balloon would be through the same port and lumen as the inner balloon.

The various sizes and shapes of the pressure balloons can be used in any of the catheter embodiments. Note that larger or smaller pressure balloons, and larger or smaller stabilizing balloons, as well as different shapes, can be used with the catheters of any of the embodiments described herein. Different shaped pressure balloons can also be utilized such as those disclosed in U.S. application Ser. No. 15/949,022, filed Apr. 20, 2018, the entire contents of which are incorporated herein by reference. Note the size of the balloons is provided by way of example and are not necessarily drawn to scale comparatively to the other components.

FIGS. 8-11 illustrate an alternate embodiment of the catheter of the present invention. The pressure balloon for detecting pressure, is designated by reference numeral 92. The outer balloon 92 functions in the same manner as pressure balloon 26 of FIG. 1 so further discussion is not warranted. That is, the discussion of the compliant balloon 26 of the embodiment of FIG. 1, i.e., compression of the outer wall of the balloon compresses the air (or other gas) within the air (or other gas) lumen, is fully applicable to balloon 92 of catheter 90 of FIGS. 8-11.

Figure 8:
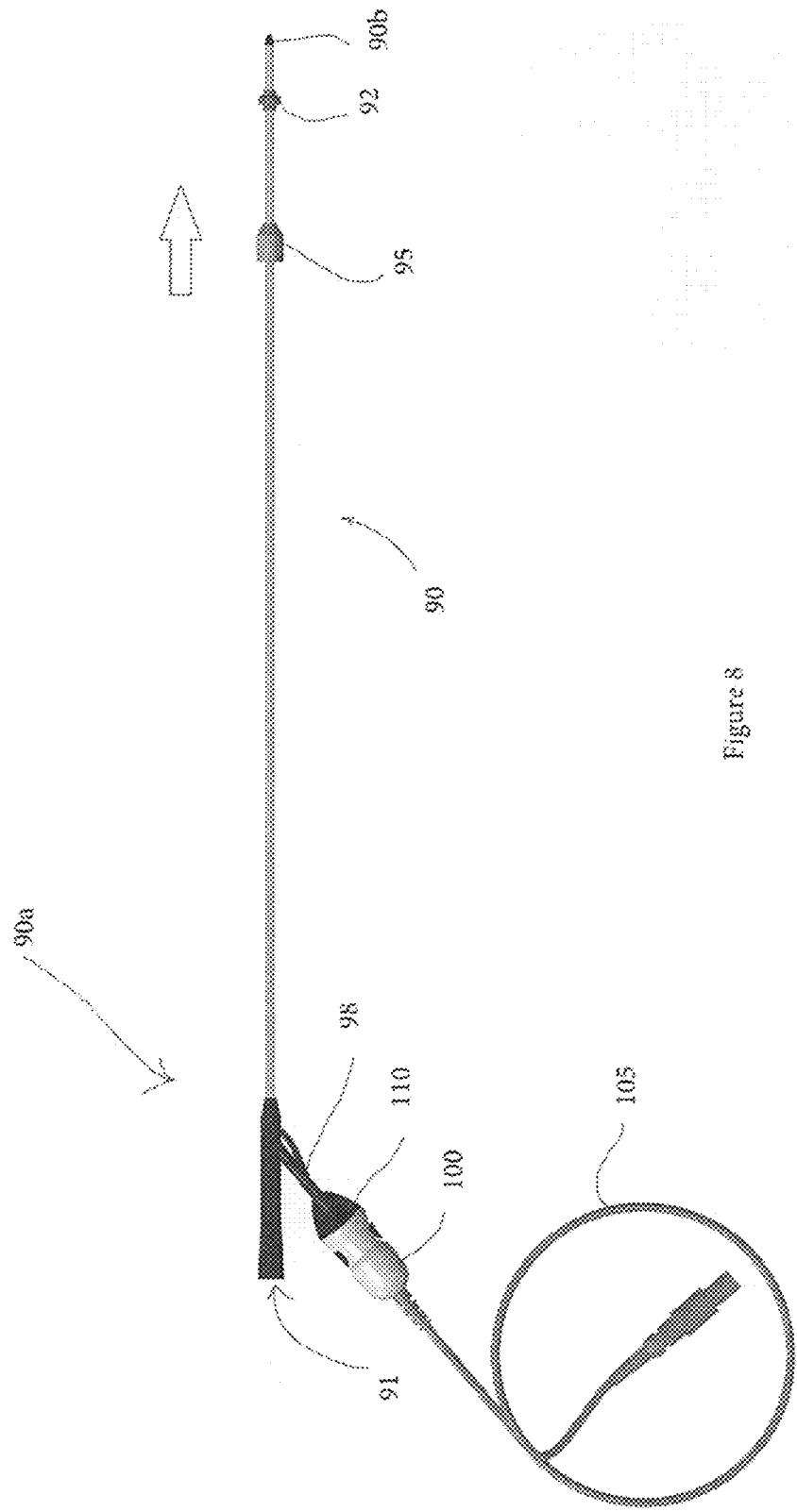
FIG. 8 is a side view of an alternate embodiment of the catheter of the present invention having a pressure balloon and a sealing member slidable along the catheter, the balloon shown in the inflated (expanded) condition and further showing the external transducer.

Note in alternate embodiments, an outer balloon can be provided so the catheter 80 would function like catheter 80 with balloons 82 and 83. That is, FIG. 8 shows the embodiment with a single pressure sensing balloon. However, the inner and outer balloons of FIG. 7A could alternatively be utilized. In such embodiment, as discussed above with regard to FIG. 7A, contained within the compliant outer balloon is a compliant inner balloon providing a smaller diameter balloon and a smaller circumference (and volume) and communicating with the gas, e.g., air lumen, to provide finer measurements as the outer balloon compresses the outer wall of the inner balloon which compresses the air within air lumen.

The pressure transducer and pressure sensor are external to catheter 90 and mounted to port 98 at the proximal end 90a of catheter 90. More specifically, a transducer hub or housing, designated generally by reference numeral 100, contains the pressure transducer and sensor and is mounted to the angled side port 98. In the embodiment of FIG. 8, the hub 100 is mounted over the port 98 and can be locked or secured thereto via connector 110 such as by a snap fit, although other attachments are also contemplated such as a friction fit, threaded attachment, a latch, etc. as well as other types of snap fits to provide an attachment that maintains an airtight seal so the air is contained within the air lumen and balloon 92. The hub 100 has an elongated (rod-like) member or nose 102 extending distally therefrom (FIGS. 9-10B) through the extension 112 of connector 110. More specifically, connector 110 is mounted to side port 98 and has a distal housing 114 from which a pair of proximally extending snap fit connector arms 116 extend. The arms 116 are sufficiently flexible to enable attachment and have an enlarged proximal portion, illustratively shown as arrow shaped although other enlarged shapes could be provided. The distal housing 114 has a lumen 118 for communication with the lumen in the side port 98 of catheter 90. The lumen 118 also communicates with the lumen 119 in the proximal extension 112 dimensioned to receive the elongated rod 102 of transducer 100. The wire for the sensor extends in housing 100. Recesses 104 in hub 100 are dimensioned to receive arms 116 when transducer hub 100 is attached to connector 110. Such attachment inserts the elongated rod 102 through seals 115a, 115b into lumen 119 and 118 to advance air though the air lumen in the catheter and into the balloon 92. (Note the air lumen extends into its angled side port 98). The elongated member 102 also has a channel 105 extending therethrough to allow the pressure wave to travel through to the pressure sensor. Although in preferred embodiments no additional air needs to be injected into balloon 92 after attachment of hub 100, it is also contemplated that a port or opening can be provided in hub 100 to receive an injection device for injection of additional air. Such additional air can communicate with and flow through channel 105 of elongated member 102, into the air lumen and balloon 92 for inflation, or alternatively, a side port or opening in angled port downstream of the elongated member 102 could be provided.

To charge the system, when the hub 100 is mounted to the side port 98 via attachment to connector 110, the elongated member 102 extends into lumens 118 and 119 to advance air through the air lumen into balloon 92 (or the inner balloon in the embodiments with inner and outer balloons) to expand the balloon 92. That is, connection of the transducer hub 100 to the catheter 90 (port 98) automatically advances air through the lumen to expand the balloon 92. In some embodiments, 0.2 cc of air can be displaced/advanced by the member 102, although other volumes are also contemplated.

Thus, as can be appreciated, mounting of the hub 100 to the catheter 90 automatically pressurizes the air lumen/chamber and expands the balloon. Note the balloon can be partially or fully inflated (expanded), dependent on the amount of air advanced into the balloon. Further note that the lumen is not vented to atmosphere when the transducer hub 100 is attached and air is advanced through the air lumen. The port 98 can include a closable seal through which the elongated member 102 is inserted but maintains the seal when the elongated member 102 remains in the lumen 104. The seal can be provided near the entry of the elongated member 102 as in the dome shaped seal (valve) 115b and seal (valve) 115a.

The lumen which is used to inflate the balloon 92 and create the air column has an opening at a distal region to communicate with the interior of inner balloon 92. If an outer balloon is provided, an additional lumen would be provided in the catheter to communicate with the outer balloon to fill the outer balloon and an additional angled port (extension) at the proximal end of catheter 90 would receive an inflation device to inflate, either fully or partially, the outer balloon.

Note as in other embodiments disclosed herein, air is described as the preferred gas for creating the column and expanding the pressure balloon, however, other gasses are also contemplated.

The balloons of the embodiments disclosed herein can be symmetrically shaped as shown or alternatively shaped such that a distal region has an outer transverse cross-sectional dimension, e.g., diameter, greater than an outer transverse cross-sectional dimension, e.g., diameter, of the proximal region. A smooth transition (taper) can be provided between the distal region and proximal region, although other configurations are also contemplated. The inner (and outer) balloon can by way of example be made of urethane, although other materials are also contemplated.

Figure 9:
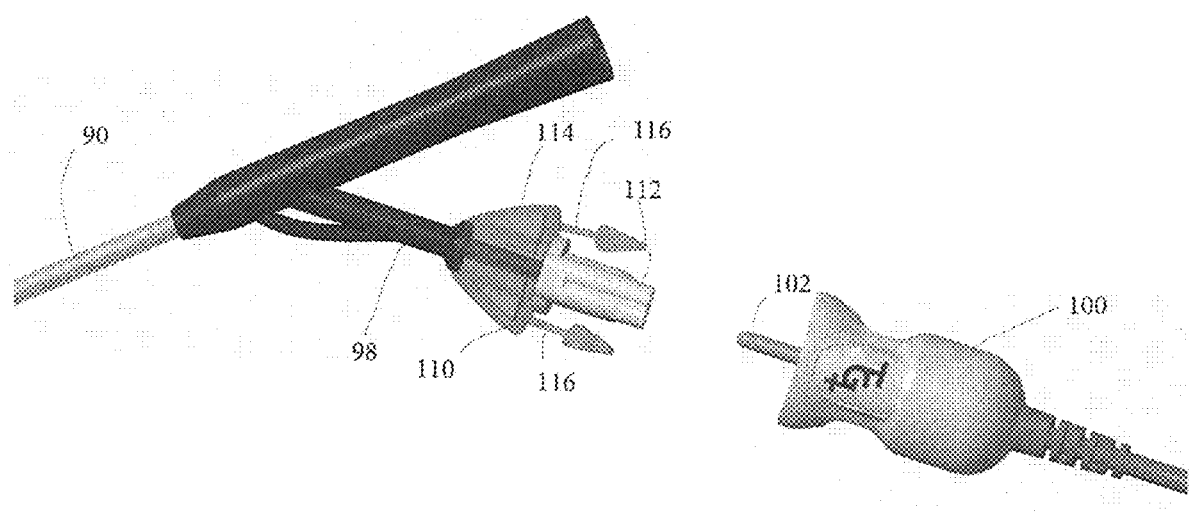
FIG. 9 is a perspective view of the proximal end of the catheter of FIG. 8 and the transducer hub prior to attachment to the catheter.
Figure 10A:
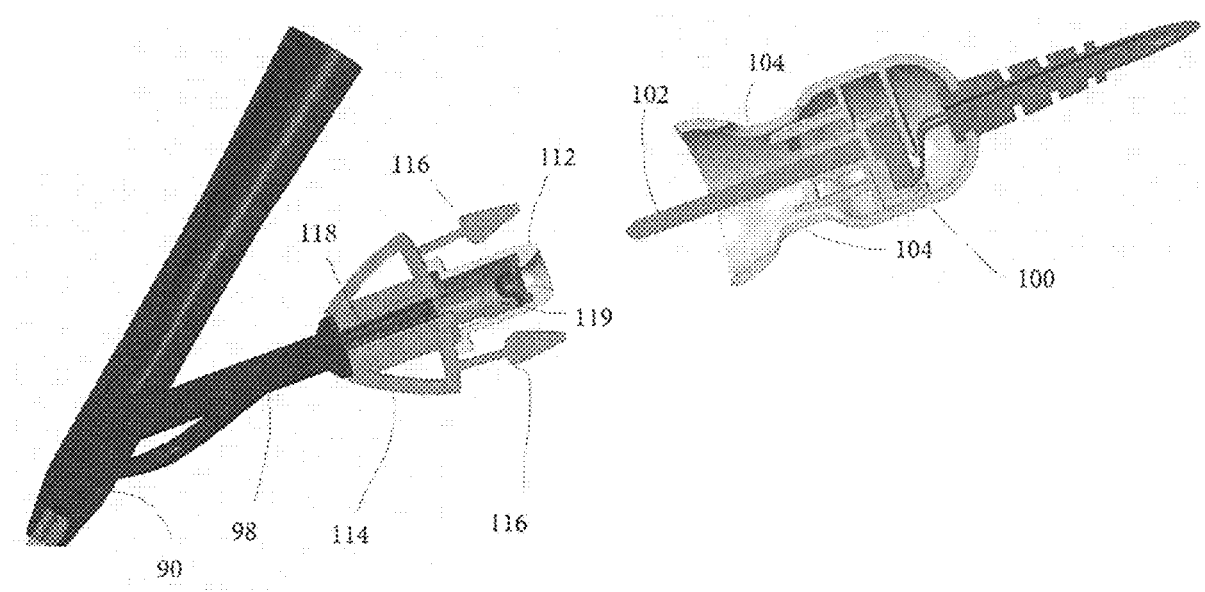
FIGS. 10A and 10B are cutaway side views showing the pressure transducer prior to connection to the catheter of FIG. 8, a portion of the hub wall and catheter connector removed to show internal components.
Figure 10B:
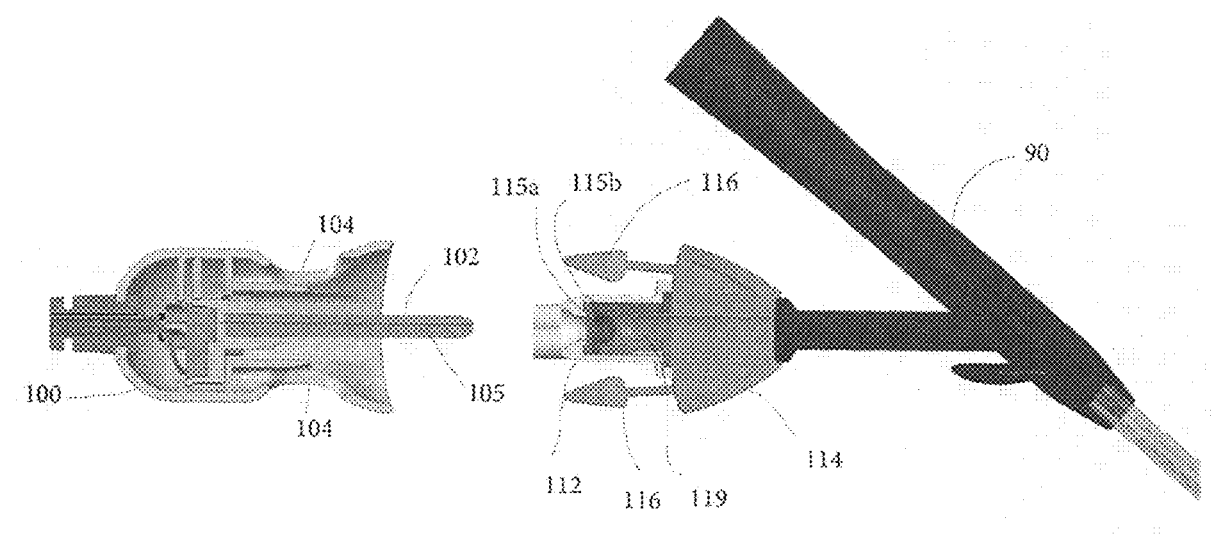
Figure 11:
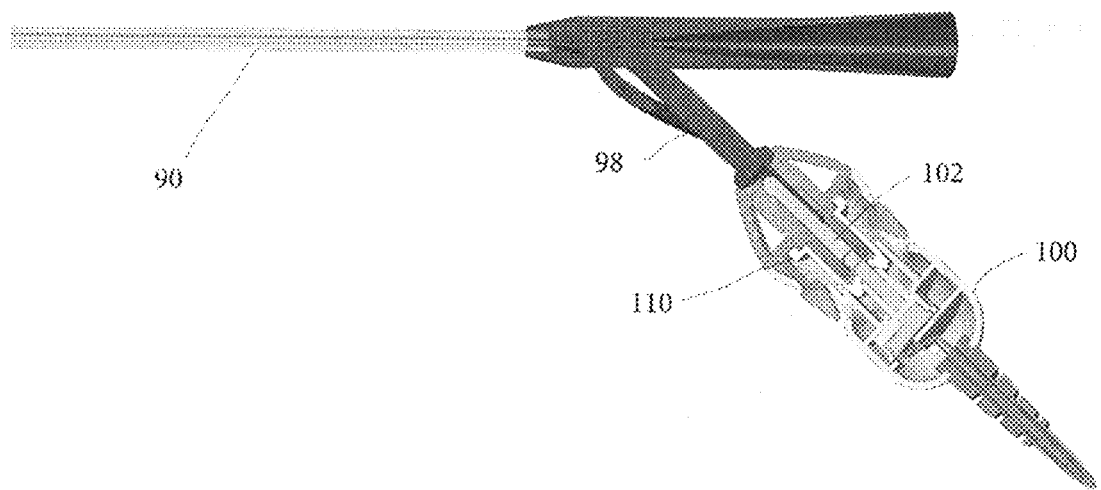
FIG. 11 is a side view showing the transducer hub attached to the catheter of FIG. 8.

In the illustrated embodiment of FIG. 9, the wire connector can plug into the openings of a connector positioned on or in the hub 100. The wire connector can be internal of the hub with an opening in the wall of the hub to enable access for the wire connector. Also note that alternatively the wire can include a female connector and the hub can have a male connector. Other types of connectors/connections are also contemplated.

Figure 5A:
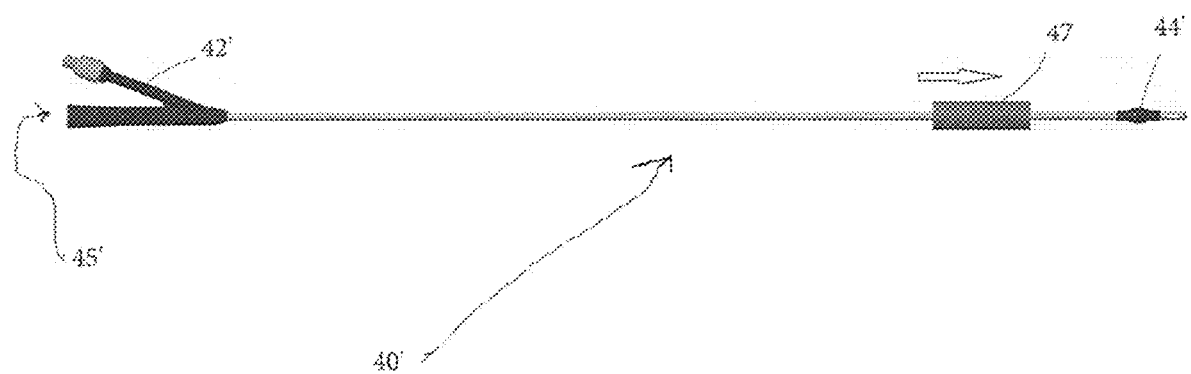
FIG. 5A is a side view of another alternate embodiment of the present invention having a slidable stopper.
Figure 5B:
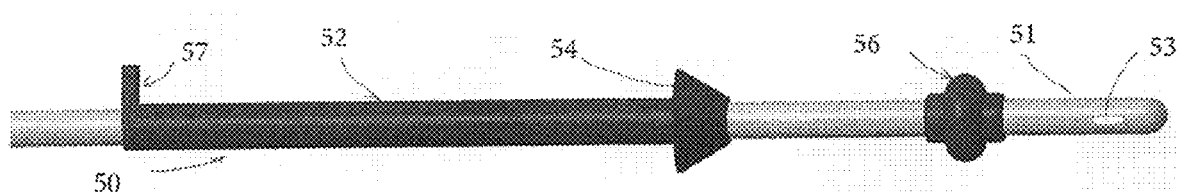
FIG. 5B is a side view of another alternate embodiment of the present invention having a stopper attached to a slidable sheath.

The catheter 90 can optionally include a slidable cork 95 for sealing the uterine cavity or alternatively a sealing balloon such as the sealing and stabilizing (retention) balloon of FIG. 5A. The stabilizing balloon, as other stabilizing balloons disclosed herein, can be made of silicone, although other materials are also contemplated. If provided, the catheter 90 would have a lumen to inflate the stabilizing balloon and an additional angled side port in communication with the lumen for injection of a liquid or gas to expand the stabilizing balloon. The foregoing description of the stabilizing balloons is fully applicable to catheter 90. Instead of a retention balloon (and the additional lumen and side port), a cork or plug can be provided to seal/prevent the outflow of dye from the uterus which in some embodiments can be slidable along the outer wall of the catheter. Catheter 90 also includes a lumen with a distal side opening 90b to provide for outflow of dye into the uterus as in the aforedescribed embodiments. In the illustrated embodiment, the opening 90b is distal of balloon 92 (and distal of the stabilizing balloon if provided which is proximal of balloon 92. In alternate embodiments, the side opening can be proximal of balloon 92 (and distal of the stabilizing balloon if provided).

Thus, in the embodiment of FIG. 8, catheter 90 has two lumens: 1) a lumen communicating with balloon 92 to inflate the balloon 92 and form the air filled chamber; and 2) lumen 91 having a side opening 90b at a distal end for injection of radiographic dye. Wires can exit from the air lumen of catheter 90 for connection to a pressure monitor via hub 100. The catheter 90, as in the foregoing embodiments, can have an atraumatic tip 90c.

In use, catheter 90 is inserted into the uterus and the cork 95 is moved along the catheter to a sealing position. The system is charged by inflation of the balloon 92, preferably partially inflated for the reasons discussed above, by advancement of air through the air lumen upon attachment of the pressure transducer 100 to the connector 110 of port 98 of catheter 90. Such attachment moves elongated member 102 into the lumen to displace the air already in the lumen to expand the balloon 92. A closed system is formed by the internal space of the balloon 92 and the internal lumen communicating with the internal space of balloon 92. In a preferred embodiment, additional air does not need to be added to the balloon 92/lumen. With the balloon 92 inflated, pressure monitoring can commence as external pressure applied to the balloon 92 compresses and deforms the balloon 92 based on changes to uterine pressure, and the pressure sensor within the external hub 100 attached at the proximal end of the catheter 90 provides continuous pressure readings, converted to an electrical signal by the transducer within the hub 100, and then electrically communicates through a connector, e.g. cable 105, to an external monitor either directly or via a converter to display pressure readings. Although the system is capable of continuous pressure monitoring, it can also be adapted if desired for periodic monitoring so the pressure readings can be taken at intervals or on demand by the clinician. As noted above, preferably no additional air needs to be added after mounting of hub 100. However, it is also contemplated that in alternate embodiments a port can be provided in communication with hub 100 to enable subsequent injection of air through the lumen 96 into balloon 92.

In the aforedescribed embodiment, mounting of the transducer hub automatically advances air through the first lumen to expand the balloon. In the alternate embodiment of FIG. 12, the pressure transducer hub 120 has a second elongated member 122 extending therefrom. When transducer hub 120 is mounted to the catheter, e.g., port 130, elongated member 102 enters the air lumen in the same manner as elongated member 102 of FIG. 11 to inflate the pressure balloon. Additionally, elongated member 122 automatically enters the lumen at port 132 which communicates with the outer balloon. Therefore, in this embodiment, the catheter has an inner and outer pressure balloon and mounting of the transducer hub 120 to the catheter a) automatically advances air through the first lumen to expand the inner balloon; and b) automatically advances air through the lumen communicating with the outer balloon to inflate (expand) the outer balloon. Side port 134 can be provided to inflate a stabilizing balloon if provided. Dye can be injected through lumen 136 to exit a distal opening in the catheter.

FIGS. 13A-13D show an alternate embodiment of the hub/connector. The pressure transducer is external to catheter 140 and mounted to port 142 at the proximal end 141 of catheter 140 via connector (housing) 150. Catheter 140 is identical to catheter 90 of FIG. 8 except for the connector and transducer hub temperature sensor connection.

Figure 13A:
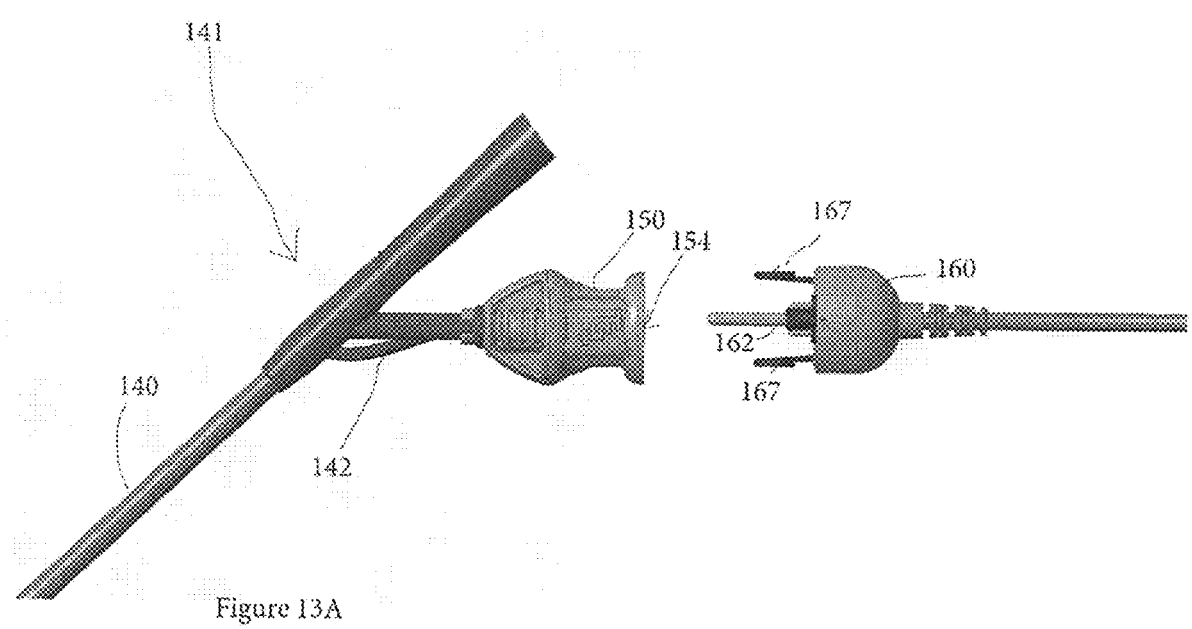
FIG. 13A is a perspective view of an alternate embodiment of the transducer hub and connector.
Figure 13B:
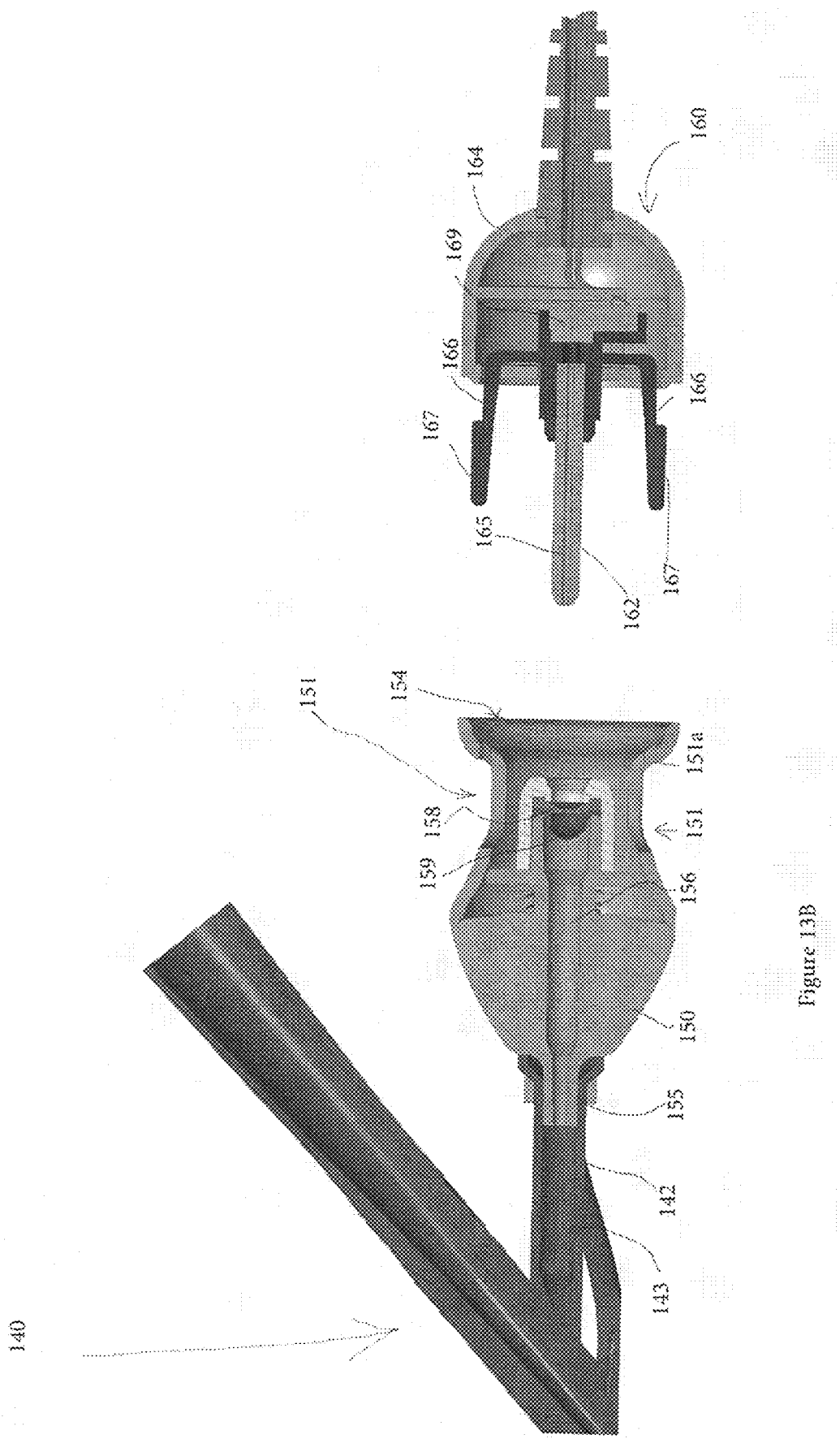
FIG. 13B is a cutaway side view of the hub and connector of FIG. 13A showing the pressure transducer prior to connection to the catheter of FIG. 13A, a portion of the hub wall and connector removed to show internal components.
Figure 13C:
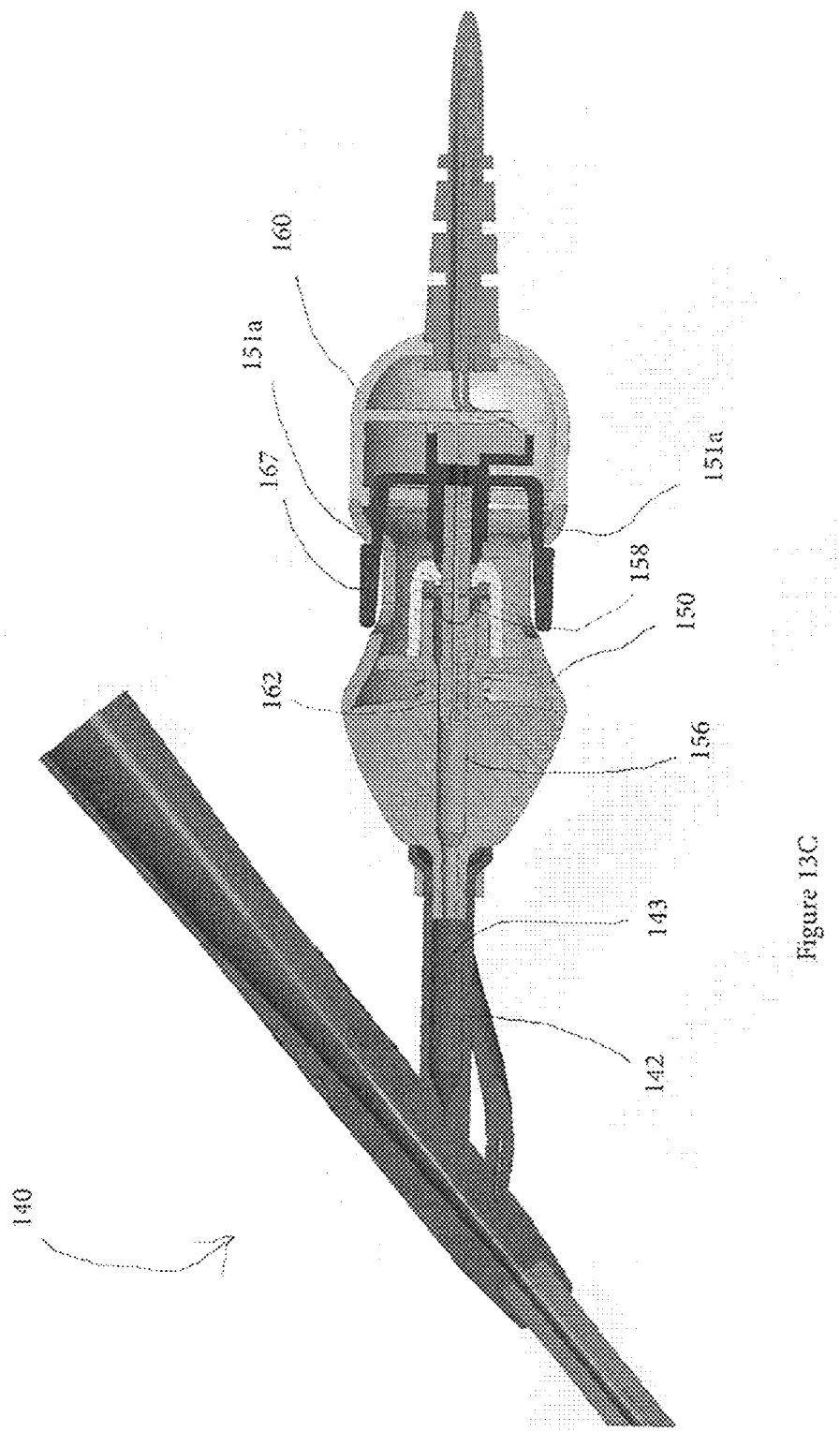
FIG. 13C is a cutaway side view similar to FIG. 13B showing the hub attached to the catheter.
Figure 13D:
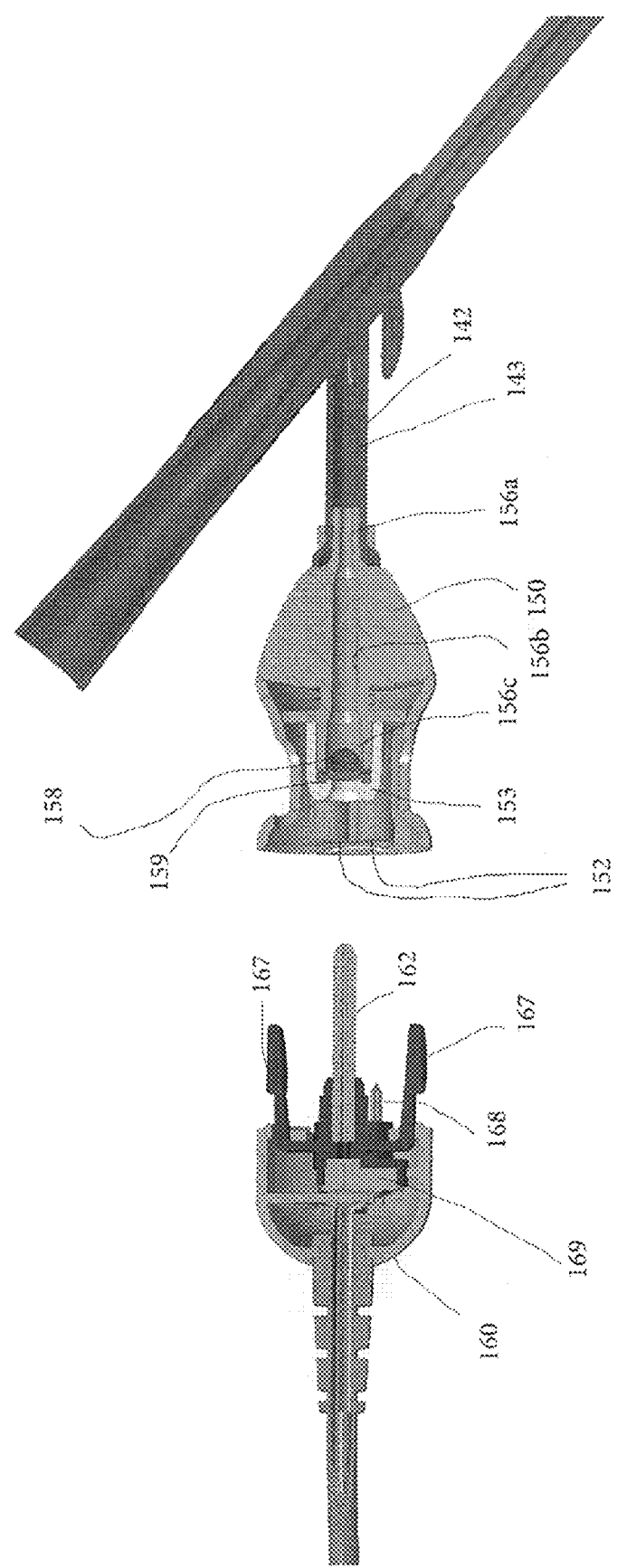
FIG. 13D is a cutaway side view similar to FIG. 13B from the other side.

More specifically, transducer hub or housing, designated generally by reference numeral 160, contains the pressure transducer and sensor 169 and is mounted to the angled side port 142. In the embodiment of FIG. 13A, the hub 160 is mounted to the catheter 140 by connection to housing 150. Housing 150 is connected to port 142 via a barbed fitting 155 providing an interference fit with the port 142. The hub 160 is locked or secured to connector 150 such as by a snap fit provided by the latch arms discussed below, although other attachments are also contemplated such as a friction fit, threaded attachment, other form of latch, etc., as well as other types of snap fits to provide an attachment that maintains an airtight seal so the air is contained within the air lumen and balloon of the catheter 140. As noted above catheter 140 is identical to catheter 90 except for its connector so catheter 140 includes a pressure balloon, stabilizing balloon, temperature sensor, etc. The catheter 140 can also have an outer and inner pressure balloon as in the aforementioned embodiments.

The housing 150 attached to catheter 140 has a proximal opening 154 and a channel (lumen) 156 to receive an elongated (rod-like) member or nose 162 extending distally from transducer hub 160. As shown channel 156 has a first diameter region 156a to match with the lumen 143 of the port 142, a second larger diameter region 156b proximal of region 156a to receive the male rod 162 of the hub 160, and a still larger diameter region 156c proximal of region 156b to receive the valve 159 and valve 158 and allow expansion thereof. As shown, valve 158 is dome shaped and is distal of valve 159. Conical cap 153, proximal of valve 159, provides a lead in to the valve 159 for the rod 162. Thermistor pins 152 receive thermistor connectors 168. Note valves 158, 159 are one example of valves that can be provided as other valves to provide an airtight seal are also contemplated. A single valve is also contemplated.

Hub 160 is mounted to connector 150 and includes a housing 164 from which a pair of distally extending snap fit connector arms 166 extend. The latch arms 166 are sufficiently flexible to enable attachment and have an enlarged distal portion 167, illustratively shown as arrow shaped although other enlarged shapes could be provided. The elongated member 162 extends between the latch arms 166. When the hub 160 is mounted to the connector 150, the elongated member 162 extends into the channel 156 to advance air to inflate the inner balloon. The enlarged ends 167 of latch arms 166 enter recesses 151 and engage shoulders 151a to retain the hub 160. Note to release (disconnect) the hub 160, the ends 167 are pressed radially inwardly to disengage from shoulder 151a and the hub 160 is pulled proximally. Note that alternatively a different number of latch arms could be provided.

The housing (connector) 150 has a lumen 156 for communication with the lumen 143 in the side port 142 of catheter 140 which communicates with the air lumen and pressure balloon of the catheter 140. As noted above, the lumen 156 is dimensioned to receive the elongated rod 162 of transducer hub 160. The wire for the sensor extends in housing 160. When transducer hub 160 is attached to connector 150, such attachment inserts the elongated rod 162 into lumen 156 to advance air though the air lumen in the catheter and into the pressure balloon. (Note the air lumen extends into its angled side port 142). The elongated member 162 also has a channel or lumen 165 extending therethrough to allow the pressure wave to travel through to the pressure sensor. Although in preferred embodiments no additional air needs to be injected into balloon 164 after attachment of hub 160, it is also contemplated that a port or opening can be provided in hub 160 to receive an injection device for injection of additional air. Such additional air can communicate with and flow through channel 165 of elongated member 162, into the air lumen and balloon 164 for inflation, or alternatively, a side port or opening in the angled port downstream (distal) of the elongated member 162 could be provided. Attachment of hub 1600 to housing 150 also automatically connects thermistor connectors 168 to thermistor pins 152 to automatically connect the temperature sensor to the hub 160 for communication via a cable to a temperature monitor.

To charge the system, when the hub 160 is mounted to the side port 142 via attachment to connector 150, the elongated member 162 extends into lumen 156 to advance air through the air lumen into the pressure balloon (or the inner pressure balloon in the embodiments with an outer balloon over the pressure balloon) to expand the balloon. That is, connection of the transducer hub 160 to the catheter 140 (port 142) automatically advances air through the connector lumen 156, the port lumen 143 and the first lumen 174 of the catheter 140 to expand the balloon. (Such connection also automatically connects the temperature sensor to the hub 160). In some embodiments, 0.2 cc of air can be displaced/advanced by the member 102, although other volumes are also contemplated. Thus, as can be appreciated, mounting of the hub 160 to the catheter 140 automatically pressurizes the air lumen/chamber and expands the balloon. Note the balloon can be partially or fully inflated (expanded), dependent on the amount of air advanced into the balloon. Further note that preferably the lumen is not vented to atmosphere when the transducer hub 160 is attached and air is advanced through the air lumen. The port 142 includes a closable seal, e.g., valves 158 and 159, through which the elongated member 162 is inserted but maintains the seal when the elongated member 162 remains in the lumen 156. Note that catheter 140 is identical in all other respects to catheter 90 so that the description of catheter 00 and its components and function (and alternatives) are fully applicable to catheter 140, the difference being the connector 150 of catheter 90 to receive transducer hub 160. The transducer hub is also different, e.g., has latch arms and a different configuration.

Additionally, in alternate embodiments, any of the catheters disclosed herein can include a channel (lumen) for sensors for measuring different parameters and their associated wires (unless wireless) can be provided in separate channels, or alternatively, one or more sensors and their associated wires can be provided in a single channel to reduce the overall size/diameter of the catheter.

It is also contemplated that a backup system be provided to determine pressure. The backup system can provide a double check of pressure readings to enhance accuracy. Such backup system can be used with any of the embodiments disclosed herein to provide a second pressure reading system. One example of such backup system has a pressure transducer/pressure sensor like sensor 30 of FIG. 1 within the air lumen communicating with the pressure balloon, forming a "first system", plus a pressure transducer/pressure sensor at a proximal end of the catheter as in FIG. 6 or external of the catheter forming a "second system". Thus, the pressure sensor is at a distal end of the air charged lumen and a pressure sensor is at proximal end of the air charged lumen. Both sensors are electrically connected to a monitor that provides a graphic display of pressure readings. A stabilizing balloon and an inflation lumen to inflate the balloon and/or a proximal plug can also be provided. A lumen provides a passage for dye in the same manner as lumen 20 of the embodiment of FIG. 1. In such embodiments, with the balloon inflated, pressure monitoring can commence as external pressure applied to an outer surface of the balloon compresses the gas, e.g., air, within the chamber.

The sensor at the distal end of the lumen provides continuous pressure readings, converted to an electrical signal by the transducer within the distal end of lumen, and then electrically communicates through its transmission wires extending through the air (or other gas) lumen to an external monitor either directly or via a converter. Additionally, pressure within the air (or other gas) charged column is measured at a proximal region by a sensor within or mounted to a side port of the catheter. The sensor at the distal end of lumen provides continuous pressure readings, and such pressure readings can be confirmed by the proximal sensor. Such pressure readings can be performed continuously or alternatively can also be adapted if desired for periodic monitoring so the pressure readings can be taken at intervals or on demand by the clinician. Thus, air (or other gas) pressure readings at a proximal end plus microtip pressure readings at the distal end are provided. The sensors can electrically communicate with an external monitor to display both pressure readings from sensors, or alternatively, if the pressure readings are different, they can be averaged to display a single measurement. Clearly, other displays of information can be provided to display the information from the two sensors.

The sensors disclosed herein can be microtip sensors within the air lumen or balloon. In alternative embodiments, fiber optic sensors within the air lumen or within or around the balloon can by utilized to transmit circumferential/area pressure exerted on the uterus. The pressure transducers can be housed within the catheter or alternatively external to the catheter.

Thus, these catheters provide a closed system. The catheters also have a balloon providing a large reservoir (large capacity) and large circumferential area/interface for obtaining more information from the uterus over multiple reference points (rather than a single point sensor) that provides an average pressure to provide a gross measurement and a more accurate assessment of the surrounding environment as pressure measurement is not limited to one side of the uterus but can determine measurements on the opposing side as well.

As noted above, the catheters, i.e. the transducer, can be connected to a bedside monitor or a handheld monitor providing a portable readout through either a wire or bluetooth wireless connection. Such wireless connection would provide the patient the option to ambulate while in labor. The monitor can be provided as a kit with one or more catheters.

The system can also include an indicator or alarm system to alert the staff at the site as well as remote staff through wired or wireless connections to external apparatus, e.g., hand held phones or remote monitors.

As noted above, an alarm or indicator can be provided in some embodiments to alert the staff. The indicator can be a visual indicator such as a light, LED, color change, etc. Alternatively, or additionally, the indicator can be an audible indicator which emits some type of sound or alarm to alert the staff. The indicator can be at the proximal region of the catheter or at other portions of the catheter, e.g., at a distal end portion, where known imaging techniques would enable the user to discern when the indicator is turned on. It is also contemplated that in addition to providing an alert to the user, the pressure or other monitoring system can be tied into a system to directly control parameters so that if the pressure or other parameter is outside a desired range, appropriate steps can be taken such as for example controlling the infusion of dye. In such systems, one or more indicators can be provided on the proximal portion of the catheter, e.g., at a proximal end outside the patient's body, or separate from the catheter. The sensor(s) is in communication with the indicator(s), either via connecting wires extending through a lumen of the catheter or a wireless connection. The sensor(s) can be part of a system that includes a comparator so that a comparison of the measured pressure, or other parameter, to a predetermined value is performed and a signal is sent to the indicator to activate (actuate) the indicator if the measured pressure value or other value is exceeded, thereby alerting the clinician or staff that pressure or other parameters are outside desired ranges and a signal is also sent to a device or system to automatically actuate the device or system to make the necessary adjustments. If the measured value is below the threshold, the indicator is not activated. It is also contemplated that microtip sensors and/or fiber optic sensors can be utilized to measure pressure, and these sensors can be utilized instead of the air pressure readings utilizing the aforedescribed balloon(s) for measuring pressure.

Although the apparatus and methods of the subject invention have been described with respect to preferred embodiments, those skilled in the art will readily appreciate that changes and modifications may be made thereto without departing from the spirit and scope of the present invention as defined by the appended claims.

What is claimed is:

1. A multi-lumen catheter for monitoring intrauterine pressure to prevent damage to fallopian tubes of a patient, the catheter comprising an elongated body configured and dimensioned for insertion into a uterus of a patient, the catheter having a first lumen, a second lumen, and a first balloon at a distal portion, the first lumen communicating with the first balloon, and the second lumen having an opening within the uterus for injection of dye or other fluid into the uterus for imaging fallopian tubes of a patient, the first balloon containing a gas to form along with the first lumen a gas containing chamber to monitor pressure within the uterus to thereby determine if excessive pressure is being applied to the fallopian tubes of the patient which could damage the fallopian tubes, and a sensor in communication with the first lumen to measure pressure about a circumferential area of the first balloon to measure pressure of the uterus to provide readings of intrauterine pressure.

2. The catheter of claim 1, wherein the gas containing chamber is a closed system.

3. The catheter of claim 1, wherein the catheter further comprises a third lumen and a second balloon positioned proximal of the first balloon for positioning outside a cervix and inside a vagina, the third lumen communicating with the second balloon to inflate the second balloon to stabilize the position of the catheter and stop outflow of dye.

4. The catheter of claim 1, further comprising a stopper slidable with respect to the catheter to stop outflow of dye from the uterus.

5. The catheter of claim 1, wherein the first balloon has a circumference engageable with a wall of the uterus at multiple contact regions to provide multiple reference points for calculation of an average pressure of the uterus and the sensor continuously measures pressure about the circumferential area of the first balloon.

6. The catheter of claim 1, further wherein the sensor is at a proximal region of the catheter, wherein the sensor continuously communicates with an external monitor to visually display pressure readings to assess if excess pressure is being exerted on the fallopian tubes of the patient based on intrauterine pressure.

7. The catheter of claim 1, wherein the first balloon contains air and after initial insertion of air to expand the first balloon, additional air does not need to be inserted during the duration of insertion of the catheter in the patient.

8. The catheter of claim 1, further comprising an outer balloon, the first balloon positioned within the outer balloon, the first balloon forming an inner balloon, the outer balloon having a circumferential area greater than a circumferential area of the inner balloon, wherein in response to pressure within the uterus exerted on an outer wall of the outer balloon, the outer balloon deforms and exerts a pressure on an outer wall of the inner balloon to deform the inner balloon and compress the gas within the inner balloon and the first lumen to provide a finer measurement, the pressure sensor measuring intrauterine pressure based on gas compression caused by deformation of the inner balloon.

9. The catheter of claim 8, further comprising a third lumen communicating with the outer balloon to inflate the outer balloon and first side port for inflation of the first balloon and a second side port for inflation of the second balloon.

10. The catheter of claim 8, further comprising an external pressure transducer connectable to the catheter and communicating with the gas filled chamber for measuring intrauterine pressure based on gas compression caused by deformation of the expanded inner balloon deformed by the expanded outer balloon.

11. The catheter of claim 10, wherein the gas is air and the pressure transducer is contained within a hub and the hub includes an elongated member extending distally therefrom, and connection of the pressure transducer to a first port of the catheter automatically inserts the elongated member into the first lumen to advance air into the inner balloon to expand the inner balloon.

12. The catheter of claim 11, wherein the first lumen is not vented to atmosphere when the pressure transducer is connected to the catheter and advances air to expand the inner balloon.

13. The catheter of claim 11, wherein the first port has a valve and the elongated member is insertable through the valve when the hub is connected to the catheter.

14. A method for determining a condition of fallopian tubes and for measuring intrauterine pressure comprising the steps of:
 providing a catheter having first and second lumens and an expandable first balloon in communication with the first lumen;
 inserting the catheter into a uterus of a patient;
 connecting a hub containing a pressure transducer to the first lumen to automatically advance air through the first lumen of the catheter to expand the first balloon to a more expanded condition;
 injecting dye or other fluid through the second lumen into the uterus to assess an open or closed condition of the fallopian tubes;
 obtaining a first pressure reading of the uterus based on deformation of the first balloon in response to pressure exerted on the first balloon; and
 transmitting the first pressure reading to an external monitor connected to the hub to indicate pressure, the indicated pressure indicative of pressure exceeding a threshold pressure which could damage the fallopian tubes.

15. The method of claim 14, further comprising a second larger balloon, wherein the first balloon is positioned within the second balloon wherein in response to pressure within the uterus exerted on a first outer wall of the expanded second balloon, the second balloon deforms and exerts a pressure on a second outer wall of the expanded first balloon to deform the first balloon and compress the air within the first balloon and the first lumen to provide a finer measurement.

16. The method of claim 14, further comprising the step of sliding a blocking member along the catheter to a position to block outflow of dye or fluid.

* * * * *